(12) United States Patent
Cheng et al.

(10) Patent No.: US 9,334,369 B2
(45) Date of Patent: May 10, 2016

(54) POLYIMIDE PRECURSOR COMPOSITION AND PREPARATION METHOD AND USE THEREOF

(71) Applicant: Eternal Materials Co., Ltd., Kaohsiung (TW)

(72) Inventors: Pi-Chen Cheng, Kaohsiung (TW); Meng-Yen Chou, Kaohsiung (TW); Chuan Zong Lee, Kaohsiung (TW); Chung-Jen Wu, Kaohsiung (TW)

(73) Assignee: Eternal Chemical Co., Ltd. (TW)

( * ) Notice: Subject to any disclaimer, the term of this patent is extended or adjusted under 35 U.S.C. 154(b) by 1 day.

(21) Appl. No.: 13/725,131

(22) Filed: Dec. 21, 2012

(65) Prior Publication Data

US 2013/0172494 A1 Jul. 4, 2013

(30) Foreign Application Priority Data

Dec. 29, 2011 (TW) .............................. 100149594 A

(51) Int. Cl.
| | | |
|---|---|---|
| C08G 73/12 | (2006.01) | |
| C07D 233/90 | (2006.01) | |
| C08G 73/10 | (2006.01) | |
| C08G 69/28 | (2006.01) | |
| C08G 69/04 | (2006.01) | |

(52) U.S. Cl.
CPC .............. C08G 73/12 (2013.01); C07D 233/90 (2013.01); C08G 73/10 (2013.01); C08G 73/1067 (2013.01); C08G 73/1071 (2013.01); C08G 69/04 (2013.01); C08G 69/28 (2013.01); C08G 73/1007 (2013.01)

(58) Field of Classification Search
CPC ..... C08G 69/04; C08G 69/28; C08G 73/1007
See application file for complete search history.

(56) References Cited

U.S. PATENT DOCUMENTS

| | | | | |
|---|---|---|---|---|
| 4,189,543 | A * | 2/1980 | Doorakian et al. | 521/128 |
| 4,323,453 | A | 4/1982 | Zampini | |
| 5,719,256 | A * | 2/1998 | Tamai et al. | 528/361 |
| 7,601,772 | B2 * | 10/2009 | Fudemoto et al. | 524/186 |
| 2001/0000259 | A1 | 4/2001 | Hall-Goulle | |
| 2008/0044683 | A1* | 2/2008 | Chan et al. | 428/626 |
| 2008/0090927 | A1* | 4/2008 | Ishii et al. | 522/47 |
| 2010/0168265 | A1 | 7/2010 | Wu et al. | |
| 2011/0086311 | A1 | 4/2011 | Katayama et al. | |

FOREIGN PATENT DOCUMENTS

| | | |
|---|---|---|
| JP | 2004-025610 A | 1/2004 |
| JP | 2007-016182 A | 1/2007 |
| JP | 2007-084798 A | 4/2007 |
| JP | 2011-080032 A | 4/2011 |
| TW | 438857 B | 6/2001 |
| TW | 201024337 A | 7/2010 |

OTHER PUBLICATIONS

ROC Taiwanese Search Report issued in corresponding ROC (Taiwan) Patent Application No. 100149594, date of completion of search Oct. 8, 2013.
Chinese First Office Action issued in corresponding Chinese Patent Application No. 201210064162.2, issued May 22, 2013.
Y. S. Vygodskii, et al., Ionic Liquids as Novel Reaction Media for the Synthesis of Condensation Polymers, Macromolecular Rapid Communication, 2002, 23, pp. 676-680.
English Translation of Japanese office action in application No. 2012-286582 mailing date Jun. 2, 2014.
English Translation of Taiwan Search Report in patent application No. 100149594 dated Oct. 8, 2013.
English translation of First Office Action for Chinese application No. 201210064162.2.
Vygodskii, Y.S., et al., "Ionic Liquids as Novel Reaction Media for the Synthesis of Condensation Polymers", Macromol. Rapid Commun., 2002, 23, pp. 676-680.

* cited by examiner

*Primary Examiner* — Gregory Listvoyb
(74) *Attorney, Agent, or Firm* — Drinker Biddle & Reath LLP

(57) ABSTRACT

The present invention provides a polyimide precursor composition comprising a polyimide precursor and a thermal base generator having the structure of formula (1):

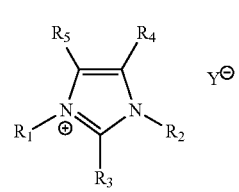

(1)

wherein $R_1$, $R_2$, $R_3$, $R_4$, $R_5$ and $Y^{\ominus}$ are as defined in the specification.
The present invention also provides a polyimide prepared from the aforementioned precursor composition, and a preparation method thereof.

26 Claims, 1 Drawing Sheet

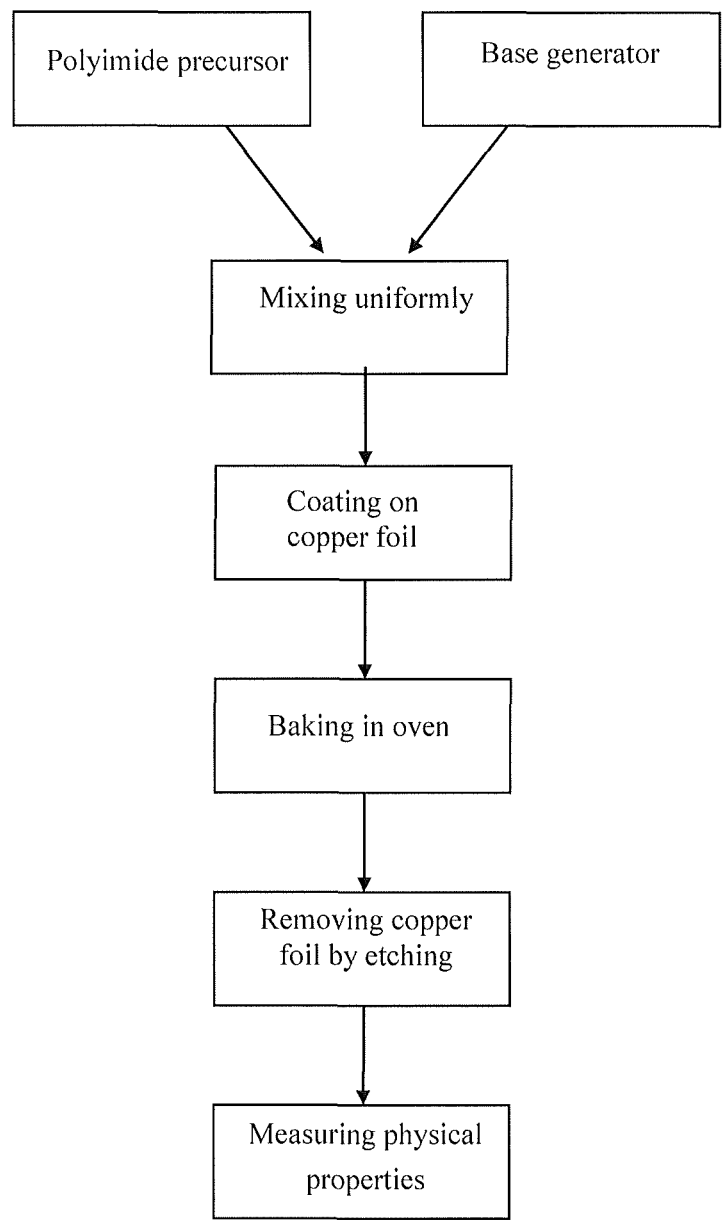

POLYIMIDE PRECURSOR COMPOSITION AND PREPARATION METHOD AND USE THEREOF

FIELD OF THE INVENTION

The present invention relates to a polyimide precursor composition, and particularly to a polyimide precursor composition comprising a thermal base generator, which can be used to prepare polyimide by low temperature imidization.

BACKGROUND OF THE INVENTION

Polyimide is the first choice among high performance polymer materials because of its excellent thermostability and desirable mechanical, electrical and chemical properties. Moreover, as requirements on semiconductor performance have become increasingly rigorous, practical limitations and deficiencies of conventional inorganic materials have grown more pronounced. These limitations and deficiencies can be offset in certain aspects by the properties of polyimide. Thus, the development of aromatic polyimide by Du Pont Corporation has attracted extensive attention, resulting in development of a variety of polyimides with multiple uses.

In the semiconductor industry, polyimides have been widely used in passive film, stress buffer film, a-particle masking film, dry etching mask, micro-electromechanical systems, interlayer insulating film, etc.; other new applications are continually being developed. Protective coating for integrated circuit devices is a predominant application, since polyimide materials have passed reliability testing for integrated circuit devices. However, polyimide is not only applied in the integrated circuit industry, but is also a key material in electronic packaging, enameled wire, printed circuit boards, sensing elements, separation film and construction materials.

Typically, polyimide is synthesized by two-stage polymerization condensation. In the first stage, a diamine monomer is dissolved in a polar, aprotic solvent such as N-methylpyrrolidone (NMP), dimethyl acetamide (DMAC), dimethyl formamide (DMF) or dimethyl sulfoxide (DMSO), and then an equimolar dianhydride monomer is added to the solution, followed by condensation at low temperature or room temperature, to form polyimide precursor, i.e., polyamic acid (PAA).

In the second stage, dehydration-condensation and cyclization reactions are carried out by thermal imidization or chemical imidization to convert polyamic acid into polyimide. To obtain a polyimide polymer with excellent electrical and physical properties typically requires heating for several hours at a high temperature of 300 to 400° C. in thermal imidization to form the highly imidized polymer. However, due to temperature restrictions inherent to some semiconductor processes, greater attention is gradually being paid to materials that can induce polyamic acid be imidized at a low temperature.

In some applications, addition of a base will promote crosslinking of monomers to cure them into a polymer. However, direct addition of the base to a formulation composition would give rise to disadvantages such as reduced storage stability. Therefore, a technique has been developed to delay the effect of the base by providing a base generator in which a base is protected by a protecting group and will be generated after the base generator is exposed to heating or irradiation of light.

Amines are commonly added as the base to catalyze low-temperature imidization. However such amine compounds are likely to catalyze imidization at room temperature. Mitsuru Ueda et al. developed a series of alkylamine thermal base generators (TBGs), as disclosed in Chemistry Letters, Vol. 34, p. 1372-1373 (2005); JP 2007056196A and Journal of Photopolymer Science and Technology, Vol. 21, No. 1, p. 125-130 (2008). Although the alkylamine thermal base generators can be used to catalyze imidization, the polyimide polymer film obtained therefrom suffers inferior thermal and mechanical properties.

The present invention represents the culmination of research and development on the problems mentioned above. The inventors of the present invention found a novel base generator which can be used in imidization for the preparation of polyimide and is effective in lowering the cyclization temperature of polyimide and improving the thermal and mechanical properties of the polyimide polymer, so as to meet demands in the industry.

SUMMARY OF THE INVENTION

An objective of the present invention is to provide a novel base generator, which can generate a base upon heating or irradiation of light. The thermal base generator or optical base generator according to the present invention can be used for imidization of polyimide precursor, promoting crosslinking of epoxy monomers, or crosslinking of polyurethane or polyurea.

Another objective of the present invention is to provide a polyimide precursor composition, which comprises a polyimide precursor and the above thermal base generator and is capable of forming polyimide by low temperature imidization.

Yet another objective of the present invention is to provide a method for preparing polyimide, which comprises polymerization of the above polyimide precursor composition by low temperature imidization.

Still another objective of the present invention is to provide a polyimide which is prepared by polymerization of the above polyimide precursor composition by low temperature imidization and has excellent thermal and mechanical properties.

BRIEF DESCRIPTION OF THE DRAWINGS

The present invention will be more fully understood from the detailed description given below, which is for illustration only, and thus is not limitative of the present invention, and wherein:

FIG. 1 is a flow chart for testing the physical properties according to the present invention.

DETAILED DESCRIPTION OF THE INVENTION

Herein, the term "alkyl" refers to saturated hydrocarbon groups, examples thereof including, but not limited to, methyl, ethyl, n-propyl, isopropyl, n-butyl, isobutyl, tert-butyl, pentyl, hexyl and the like. The term "aryl" refers to aromatic ring systems of 6-carbon monocyclic ring, 10-carbon bicyclic ring or 14-carbon tricyclic ring, examples thereof including, but not limited to, phenyl, tolyl, naphthyl, fluorenyl, anthryl, phenanthryl and the like. The term "haloalkyl" refers to alkyl substituted with halogen, wherein "halogen" means fluorine, chlorine, bromine or iodine, preferably fluorine or chlorine. The term "alkoxy" refers to alkyl attached to oxygen atom, examples thereof including, but not limited to, methoxy, ethoxy, propoxy, isopropoxy, n-butoxy, isobutoxy, pentyloxy, hexyloxy, benzyloxy, fluorenylmethoxy and the like.

The base generator according to the present invention has the structure of formula (1):

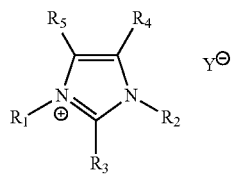

wherein
- $R_1$ and $R_2$ are the same or different and are each independently H, linear or branched $C_1$-$C_6$ alkyl, linear or branched $C_1$-$C_6$ haloalkyl, or linear or branched $C_1$-$C_6$ alkyl substituted with one or more $C_6$-$C_{14}$ aryl,

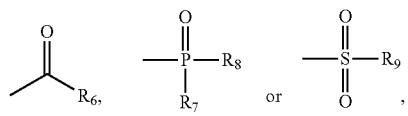

wherein
- $R_6$ is linear or branched $C_1$-$C_6$ alkyl, linear or branched $C_1$-$C_6$ haloalkyl, linear or branched $C_1$-$C_8$ alkoxy unsubstituted or substituted with one or more $C_6$-$C_{14}$ aryl, or —$NR_{10}R_{11}$, and
- $R_7$, $R_8$, $R_9$, $R_{10}$ and $R_{11}$ are the same or different, and are each independently H, linear or branched $C_1$-$C_4$ alkyl unsubstituted or substituted with one or more $C_6$-$C_{14}$ aryl, or $C_6$-$C_{14}$ aryl;
- $R_3$, $R_4$ and $R_5$ are the same or different, and are each independently H, linear or branched $C_1$-$C_6$ alkyl unsubstituted or substituted with one or more $C_6$-$C_{14}$ aryl, linear or branched $C_1$-$C_6$ hydroxyalkyl, linear or branched $C_1$-$C_6$ cyanoalkyl, or $C_6$-$C_4$ aryl; and
- $Y^{\ominus}$ is an anionic group.

According to an embodiment of the present invention, the groups $R_1$ and $R_2$ in formula (1) are the same or different and are each independently linear or branched $C_1$-$C_6$ alkyl,

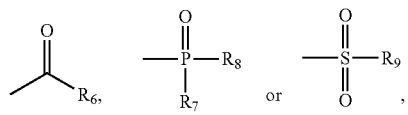

wherein
- $R_6$ is linear or branched $C_1$-$C_6$ alkyl, linear or branched $C_1$-$C_6$ haloalkyl, linear or branched $C_1$-$C_8$ alkoxy unsubstituted or substituted with one or more $C_6$-$C_{14}$ aryl, or —$NR_{10}R_{11}$; and $R_7$, $R_8$, $R_9$, $R_{10}$ and $R_{11}$ are the same or different and are each independent H, linear or branched $C_1$-$C_{14}$ alkyl, or $C_6$-$C_{14}$ aryl. Preferably, $R_6$ is methyl, ethyl, n-propyl, isopropyl, n-butyl, isobutyl, tert-butyl, pentyl, hexyl, trifluoromethyl, pentafluoethyl, methoxy, ethoxy, propoxy, butoxy, pentyloxy, hexyloxy, benzyloxy and fluorenylmethoxy; and $R_7$, $R_8$, $R_9$, $R_{10}$ and $R_{11}$ are each independently H, methyl, ethyl, n-propyl, isopropyl, n-butyl, isobutyl, tert-butyl, pentyl, hexyl, heptyl, octyl, phenyl, benzyl or diphenyl methyl.

According to an embodiment of the present invention, the groups $R_1$ and $R_2$ in formula (1) are the same or different and are each independently methyl, ethyl, propyl, butyl or selected from a group consisting of:

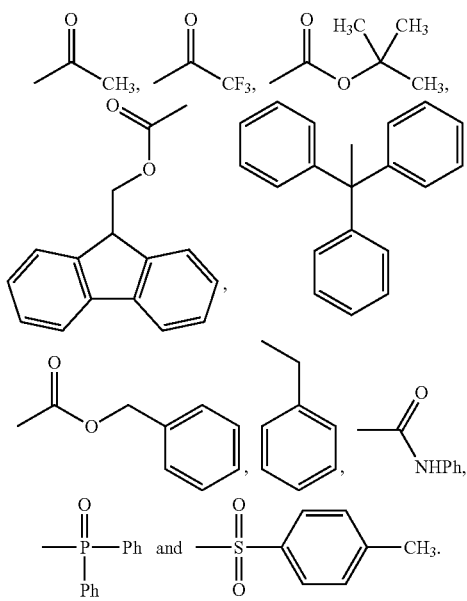

Preferably, $R_1$ and $R_2$ are the same or different and are each independently methyl, ethyl or selected from a group consisting of:

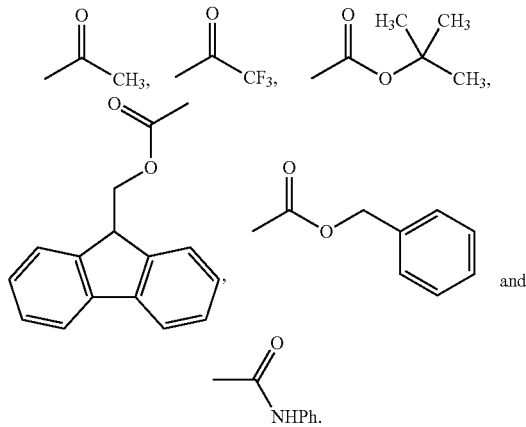

According to an embodiment of the present invention, $R_3$, $R_4$ and $R_5$ in formula (1) are the same or different and are each independently H, methyl, ethyl, n-propyl, isopropyl, n-butyl, isobutyl, tert-butyl, pentyl, hexyl, hydroxymethyl, hydroxyethyl, hydroxypropyl, hydroxybutyl, hydroxypentyl, hydroxyhexyl, cyanomethyl, cyanoethyl, cyanopropyl, cyanobutyl, cyanopentyl, cyanohexyl, phenyl, benzyl or diphenylmethyl; preferably, hydroxybutyl is selected from a group consisting of

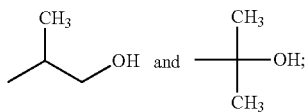

preferably, hydroxypentyl is selected from a group consisting of

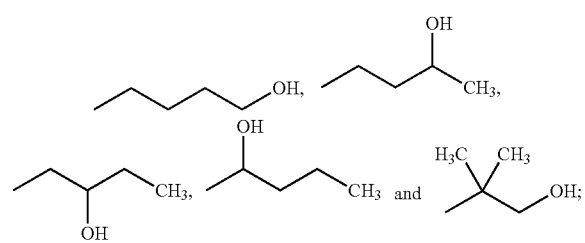

preferably, cyanobutyl is selected from a group consisting of

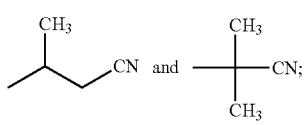

and preferably, cyanopentyl is selected from a group consisting of

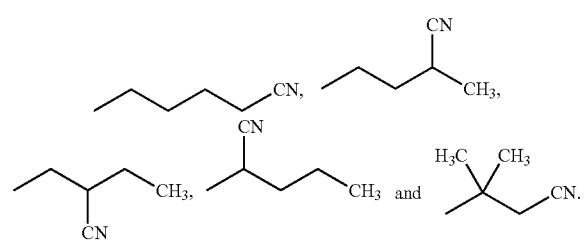

Preferably, $R_3$, $R_4$ and $R_5$ are the same or different and are each independently H, methyl, ethyl, n-propyl or isopropyl.

The anionic group in formula (1) is not particularly limited, examples thereof including, but not limited to, halide ion, sulfate, nitrate, phosphate, sulfonate, carbonate, tetrafluoborate, borate, chlorate, iodate, hexafluorophosphate, perchlorate, trifluoromethanesulfonate, trifluoroacetate, acetate, tert-butylcarbonate, $(CF_3SO_2)_2N^-$ or tert-butyloxy. According to an embodiment of the present invention, the anionic group in formula (1) is halide ion or tetrafluoborate. Preferably, the halide ion is fluoride ion and chloride ion.

The base generator according to the present invention can be prepared by any methods known in the art. For example, it may be prepared by dissolving an imidazole compound in a solvent under nitrogen, and reacting with anhydrides, isocyanates, alkylhalides, aromatics, sulfonic acids, acyl chlorides or phosphoric acids, followed by purification to obtain the base generator of the present invention.

The base generator according to the present invention can be used as an optical base generator or thermal base generator, preferably a thermal base generator which can be used for preparing polyimide by low temperature imidization, promoting crosslinking of epoxy monomers, or crosslinking of polyurethane or polyurea. In the present invention, the low temperature imidization is carried out at a temperature of not higher than 250° C., preferably not higher than 200° C.

The present invention also provides a polyimide precursor composition comprising (a) a polyimide precursor and (b) the thermal base generator having the structure of formula (1).

In the precursor composition according to the present invention, the polyimide precursor is not particularly limited, and includes those which can be readily selected by persons skilled in the art. Preferably, the polyimide precursor is selected from a group consisting of:

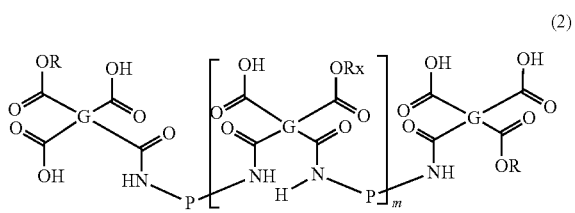

(2)

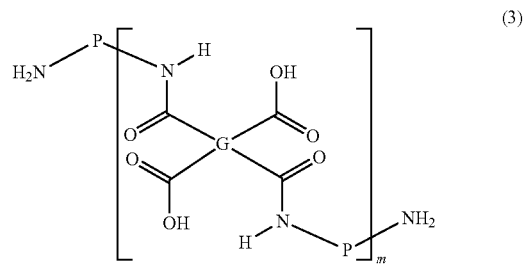

(3)

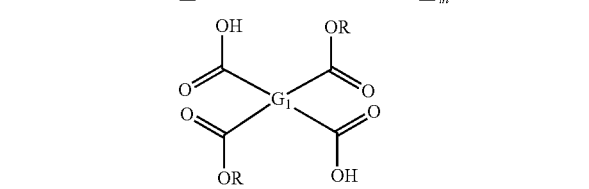

(4)

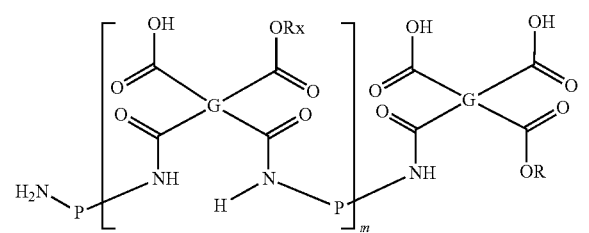

(5)

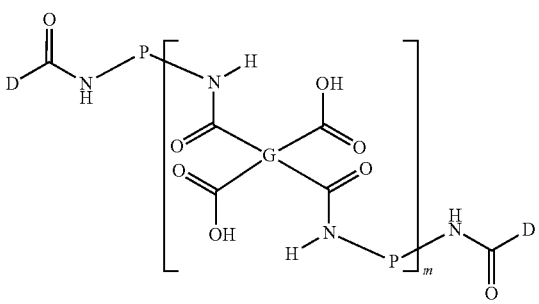

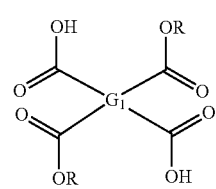

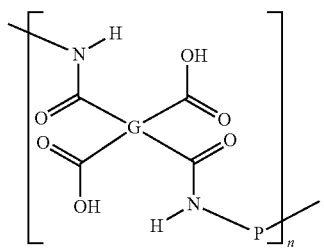

wherein,

G and $G_1$ are the same or different and are each independently a tetravalent organic group;

each P independently represents a divalent organic group;

each R independently represents linear or branched $C_1$-$C_{14}$ alkyl, $C_6$-$C_{14}$ aryl, $C_6$-$C_{14}$ aralkyl, a phenolic group or an ethylenically unsaturated group;

each $R_x$ independently represents H or an ethylenically unsaturated group;

each D independently represents a nitrogen-containing heterocyclic group or a OR* group, wherein R* is linear or branched $C_1$-$C_{20}$ alkyl;

each m is an integer from 0 to 100; and each n is an integer greater than 0.

In the precursor composition according to the present invention, a weight ratio of component (a) to component (b) ranges from 2000:1 to 5:1, preferably 1000:1 to 10:1, and more preferably 200:1 to 10:1.

According to an embodiment of the present invention, the ethylenically unsaturated group is not particularly limited, examples thereof including, but not limited to, ethenyl, propenyl, methylpropenyl, n-butenyl, isobutenyl, ethenylphenyl, propenylphenyl, propenyloxymethyl, propenyloxyethyl, propenyloxypropyl, propenyloxybutyl, propenyloxypentyl, propenyloxyhexyl, methylpropenyloxymethyl, methylpropenyloxyethyl, methylpropenyloxypropyl, methylpropenyloxybutyl, methylpropenyloxypentyl, methylpropenyloxyhexyl, a group of the following formula (7) and a group of the following formula (8):

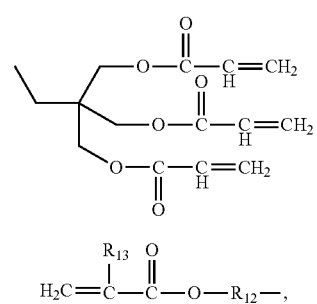

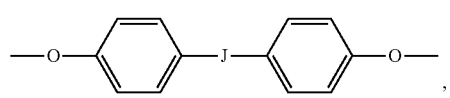

wherein $R_{12}$ is a phenylene, linear or branched $C_1$-$C_8$ alkylene, linear or branched $C_2$-$C_8$ alkenylene, $C_3$-$C_8$ cycloalkylene, or linear or branched $C_1$-$C_8$ hydroxylalkylene; and $R_{13}$ is hydrogen or linear or branched $C_1$-$C_4$ alkyl. Among others, the preferred group of formula (8) is selected from a group consisting of:

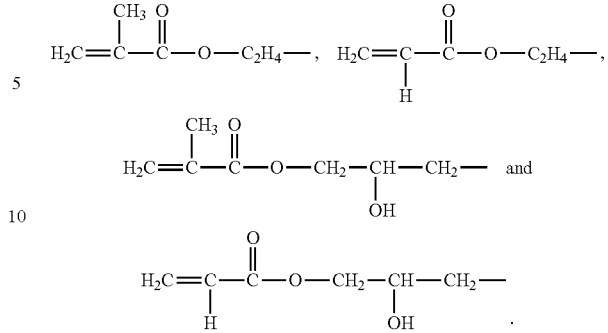

According to an embodiment of the present invention, the tetravalent organic groups G and $G_1$ are not particularly limited, examples thereof including, but not limited to, tetravalent aromatic groups or tetravalent aliphatic groups. The aromatic groups can be monocyclic or polycyclic rings, preferably selected from a group consisting of:

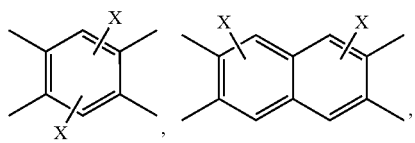

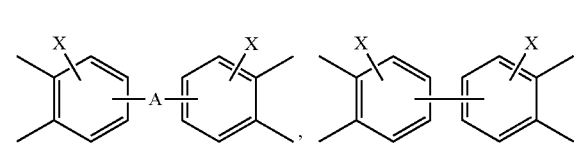

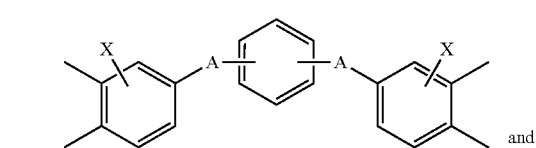

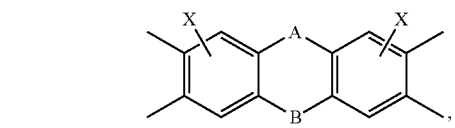

wherein X is each independently hydrogen, halogen, linear or branched $C_1$-$C_4$ perfluoroalkyl or linear or branched $C_1$-$C_4$ alkyl, and A and B are each independently a covalent bond, linear or branched $C_1$-$C_4$ alkyl, linear or branched $C_1$-$C_4$ perfluoroalkyl, alkoxy, silanyl, oxygen, sulfur, carbonyl, carboxylate, sulfonyl, phenyl, biphenyl, or

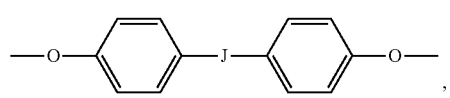

wherein J is —O—, —$SO_2$—, —$CH_2$—, $C(CF_3)_2$ or $C(CH_3)_2$.

More preferably, the tetravalent organic groups G and $G_1$ are each independently selected from a group consisting of:
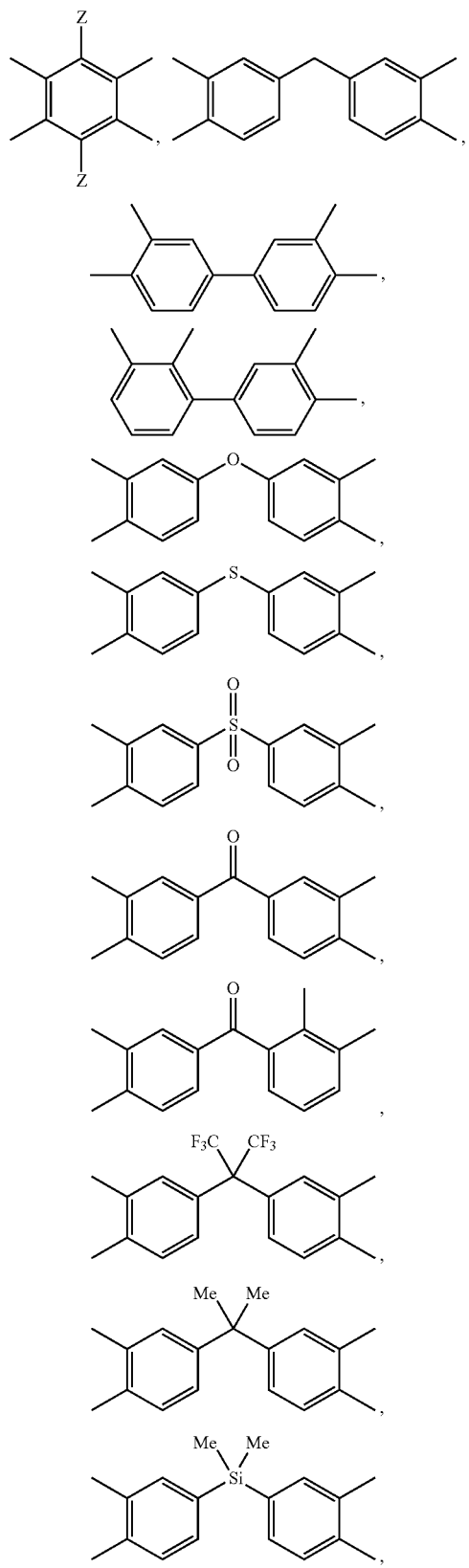
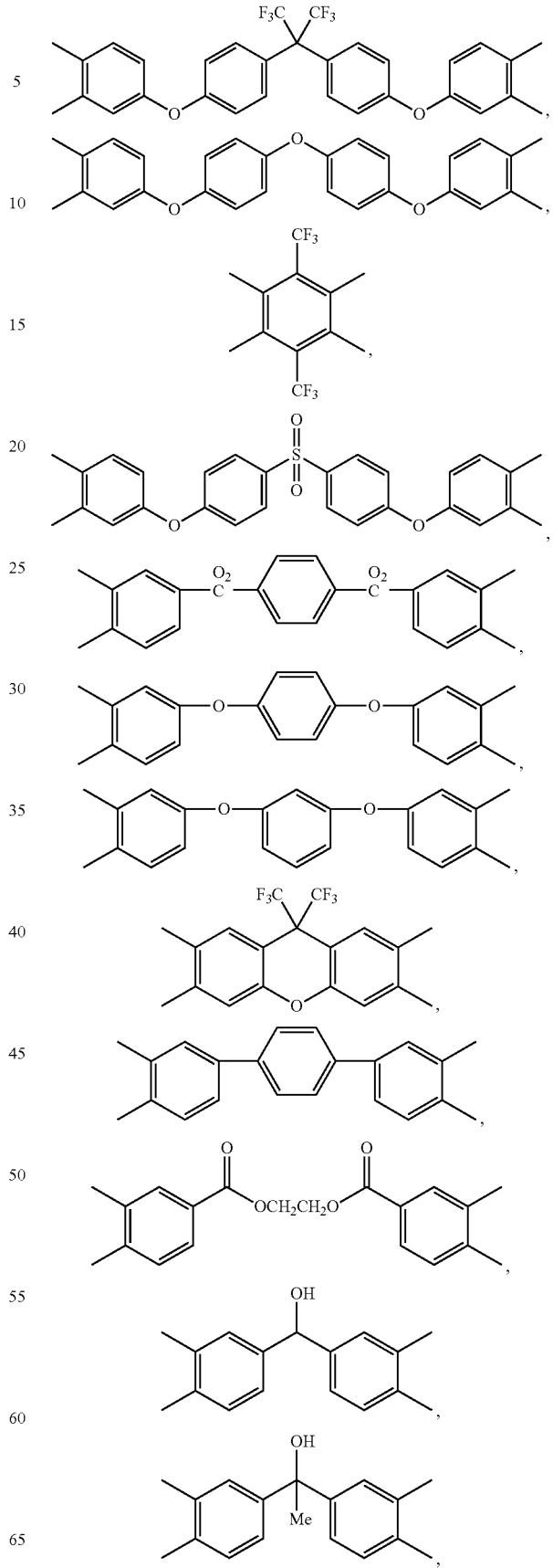

-continued

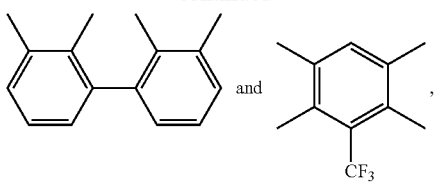

wherein Z is hydrogen or halogen.

Most preferably, the tetravalent organic groups G and $G_1$ are each independently:

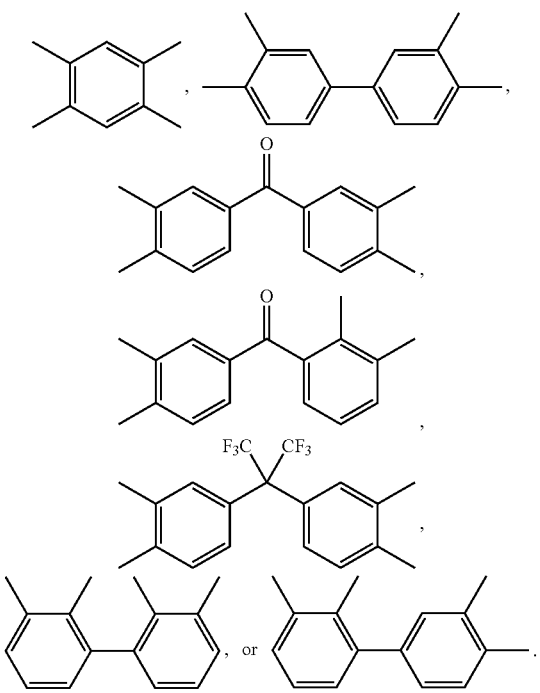

According to an embodiment of the present invention, the tetravalent aliphatic groups are selected from a group consisting of:

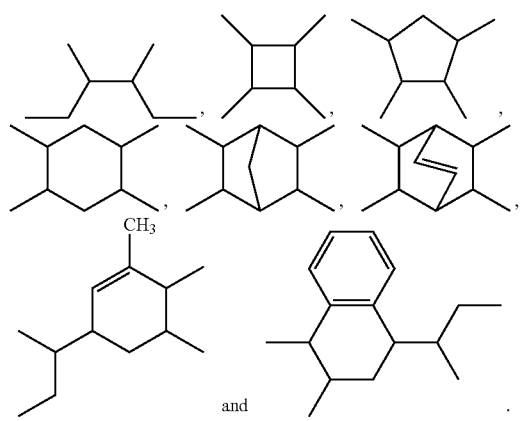

According to an embodiment of the present invention, the divalent organic group P is not particularly limited, such as, but not limited to, an aromatic group. Preferably, the divalent organic group P is each independently selected from a group consisting of:

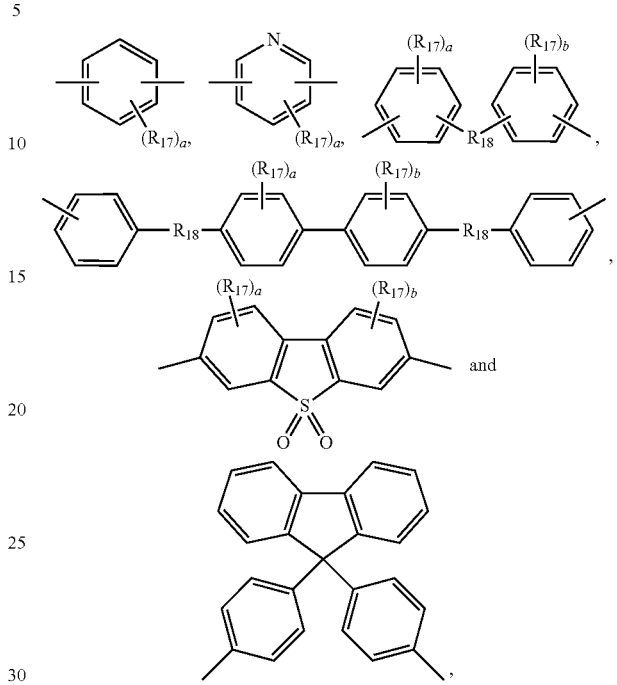

wherein, $R_{17}$ is each independently H, $C_1$-$C_4$ alkyl, $C_1$-$C_4$ perfluoroalkyl, methoxy, ethoxy, halogen, OH, COOH, $NH_2$ or SH;

each a is independently an integer of 0 to 4;

each b is independently an integer of 0 to 4; and $R_{18}$ is a covalent bond or a group selected from:

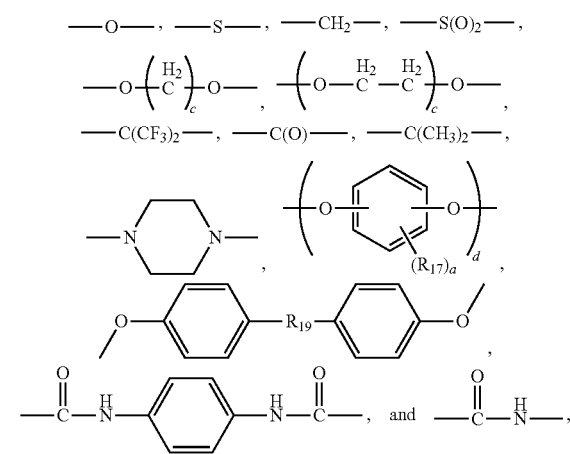

wherein, c and d are each independently an integer from 0 to 20;

$R_{17}$ and a are as defined above; and $R_{19}$ is —$S(O)_2$—, —C(O)—, a covalent bond or linear or branched $C_1$-$C_{18}$ alkyl.

More preferably, each divalent organic group P is independently selected from a group consisting of:
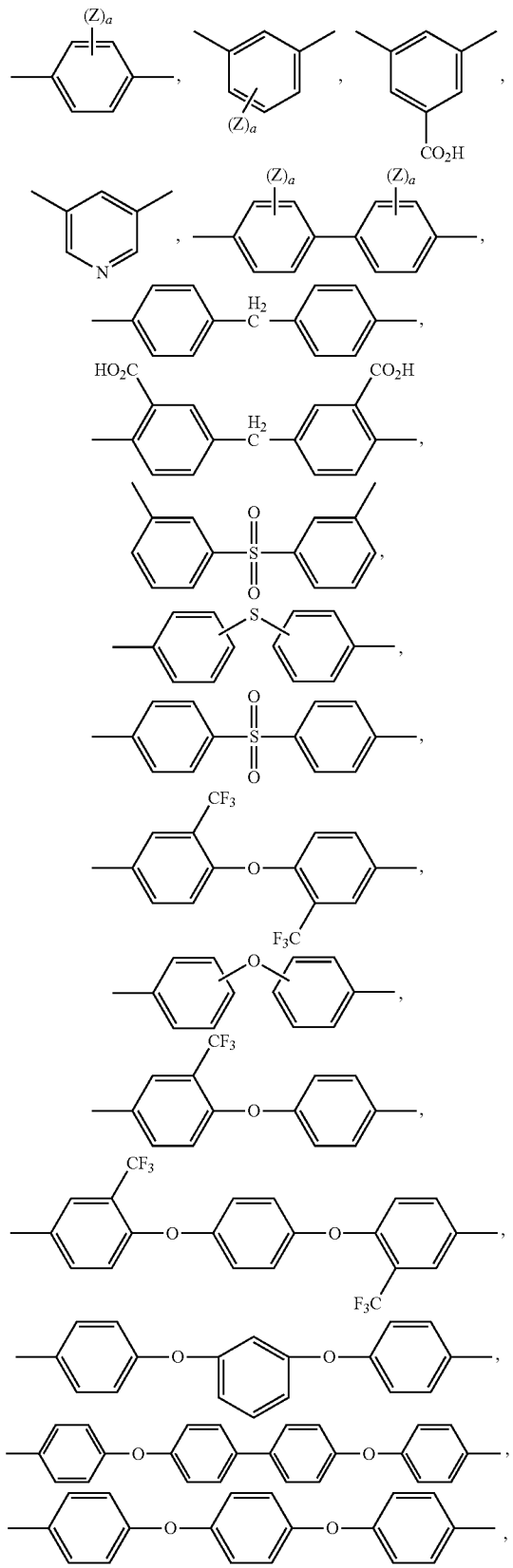
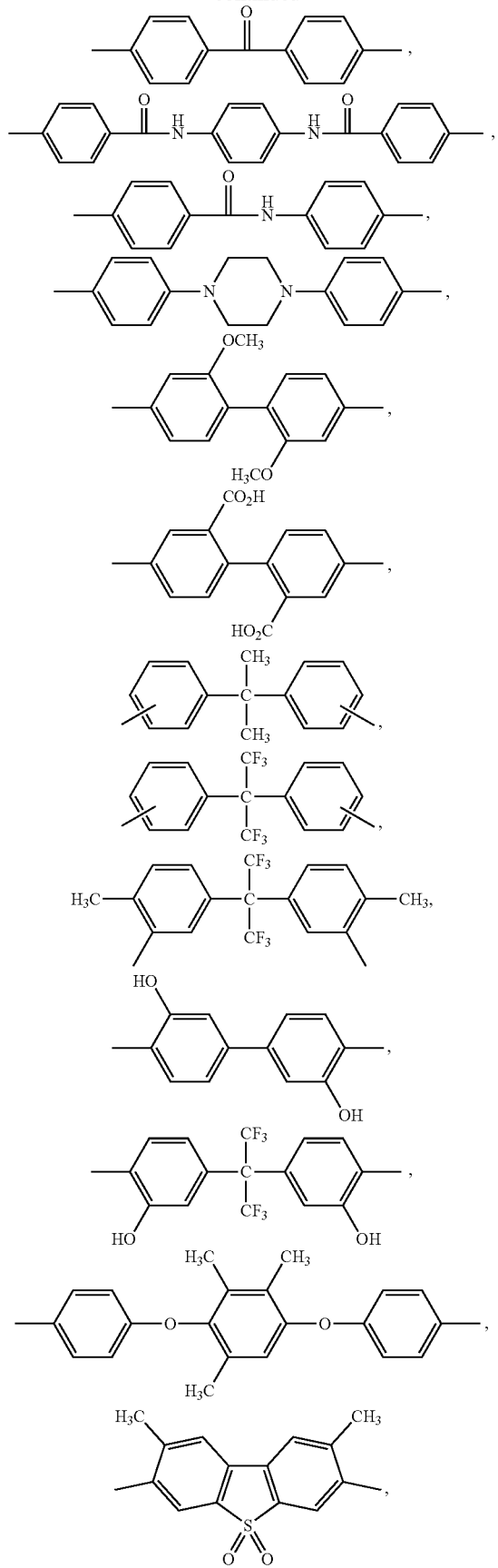

-continued

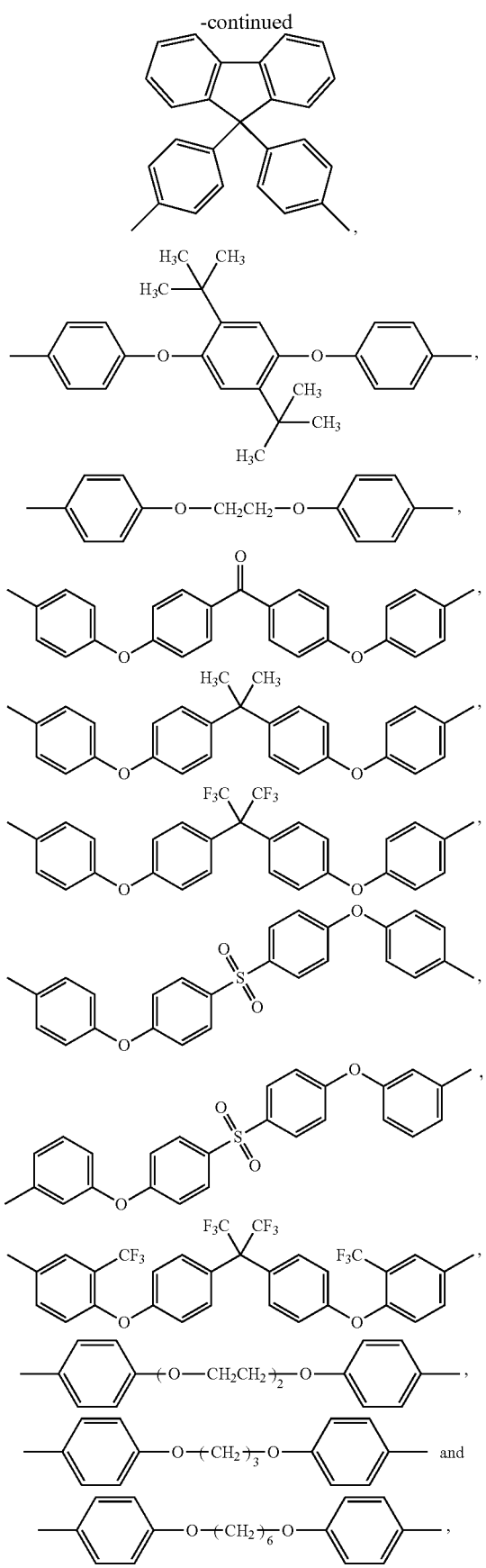

wherein
each of a is independently an integer of 0 to 4; and
each Z is independently hydrogen, methyl, trifluoromethyl or halogen.

Most preferably, each divalent organic group P is independently

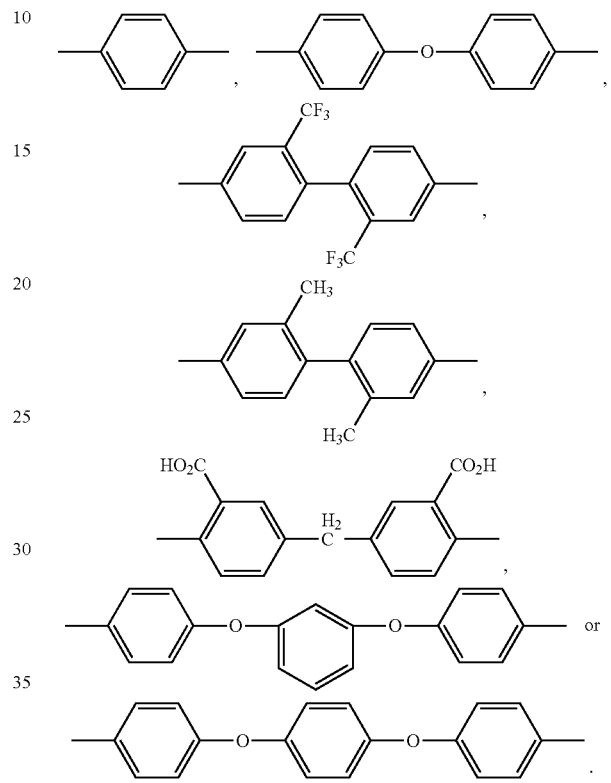

The divalent organic group P can also be a non-aromatic group, for example, but not limited to:

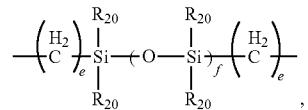

wherein each $R_{20}$ is independently H, methyl or ethyl; and e and f are each independently an integer greater than 0.

Preferably, the 2-valent organic group P is

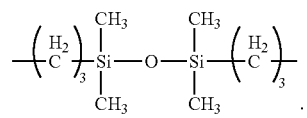

In the polyimide precursors of formulae (2) to (5), each R is independently linear or branched $C_1$-$C_{14}$ alkyl, $C_6$-$C_{14}$ aryl, $C_6$-$C_{14}$ aralkyl, a phenolic group or an ethylenically unsaturated group. The linear or branched $C_1$-$C_{14}$ alkyl is exemplified by, but not limited to, the following groups:

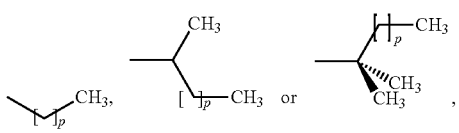

wherein p is an integer from 0 to 10. For example, the linear or branched $C_1$-$C_{14}$ alkyl may be methyl, ethyl, n-propyl, isopropyl, 1-methylpropyl, 2-methylpropyl, n-butyl, isobutyl, tert-butyl, 1-methylbutyl, 2-methylbutyl, pentyl, hexyl, heptyl or octyl. The ethylenically unsaturated group is as defined above. The $C_6$-$C_{14}$ aryl or $C_6$-$C_{14}$ aralkyl mentioned above is preferably selected from a group consisting of:

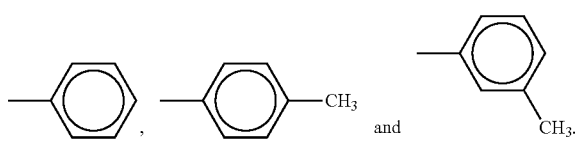

R is most preferably selected from a group consisting of:

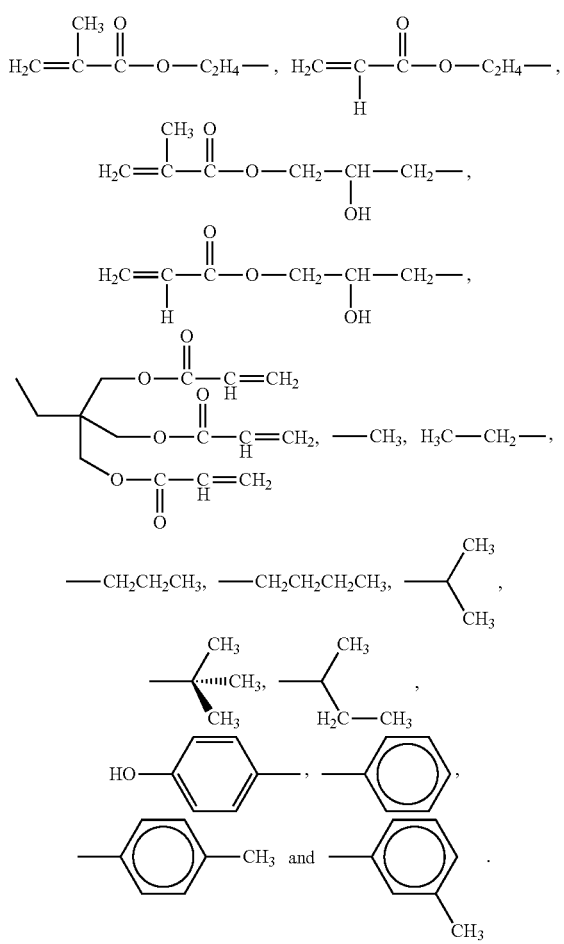

In the polyimide precursors of formulae (2) and (4), each $R_x$ is independently H or an ethylenically unsaturated group, wherein the ethylenically unsaturated group is as defined above. According to the present invention, preferably each of the group $R_x$ is independently H, 2-hydroxypropyl methacrylate, ethyl methacrylate, ethyl acrylate, propenyl, methylpropenyl, n-butenyl or isobutenyl, more preferably H or 2-hydroxypropyl methacrylate of formula below:

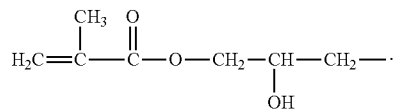

In the polyimide precursors of formula (5), the group D is each independently an nitrogen-containing heterocyclic group or an OR*-containing group, wherein R* is linear or branched $C_1$-$C_{20}$ alkyl. According to the present invention, the term "the nitrogen-containing heterocyclic group" refers to a non-aromatic 5 to 8-membered monocyclic ring having 1 to 3 heteroatoms, a 12-membered bicyclic ring having 1 to 6 heteroatoms, or a 11 to 14-membered tricyclic ring having 1 to 9 heteroatoms (in which the heteroatoms are nitrogen), examples thereof including, but not limited to, pyridyl, imidazolyl, morpholinyl, piperidyl, piperazinyl, pyrrolidinyl, pyrrolidinonyl and the like. Preferably, the each group D is independently:

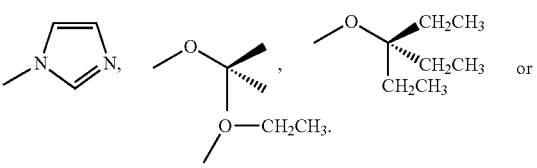

According to an embodiment of the present invention, m in the polyimide precursors of formulae (2) to (5) is an integer from 0 to 100, preferably 5 to 50, more preferably 5 to 25; and n in the polyimide precursor of formula (6) is an integer of higher than 0, preferably an integer from 1 to 1000.

In the present invention, the precursor composition can further include a solvent, preferably a polar aprotic solvent. For example, the aprotic solvent can be selected from a group consisting of N-methylpyrrolidone, dimethyl acetamide, dimethyl formamide, dimethyl sulfoxide, toluene, xylene, propylene glycol methyl ether (PGME), propylene glycol methyl ether acetate (PGMEA), γ-butyrolactone (GBL), tetraethylene glycol dimethyl ether (TGDE) and a combination thereof.

The precursor composition according to the present invention may optionally include some additives that are known in the art for the preparation of polyimide, for example, a leveling agent, a defoaming agent, a coupling agent, a dehydrating agent, a catalyst, an optical initiator, and etc.

The present invention also provides a method for polymerization of the precursor composition by low temperature imidization and a polyimide obtained therefrom. The method comprises polymerization of the aforementioned precursor composition by low temperature imidization. In an embodiment of the present invention, the low temperature imidization is carried out at a temperature of not higher than 250° C., preferably not higher than 200° C. For example, the method for preparing polyimide comprises:

1. Polymerization of Polyimide Precursor

As exemplified by the polyimide precursor of formula (4), the polymerization scheme includes:

(a) reacting a dianhydride of formula (9) with a compound having hydroxyl (R—OH) to form a compound of formula (10);

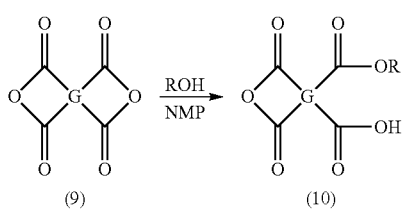

(b) adding a diamine compound of formula H₂N—P—NH₂ to the product obtained from step (a), to form an amic acid ester oligomer of formula (11); and

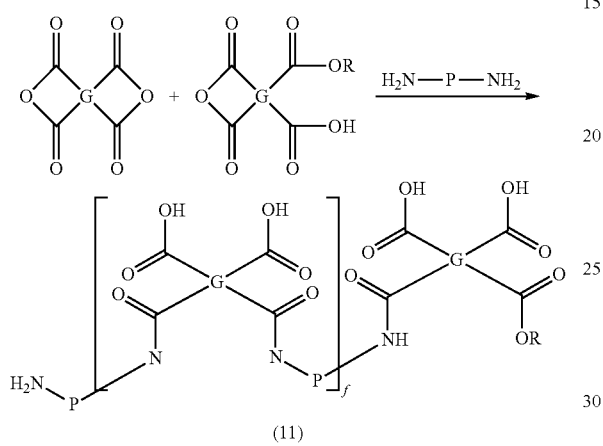

(c) optionally incorporating a monomer having a photosensitive polymerizable group ($R_x$), such as epoxy acrylate, for carrying out reaction to form the polyimide precursor of formula (12)

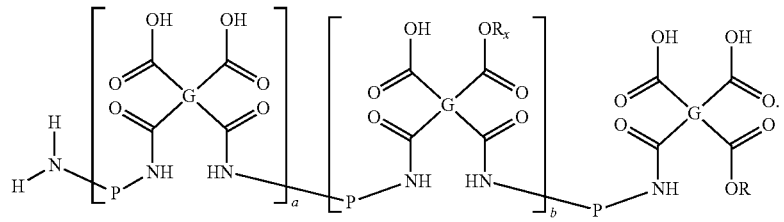

2. Preparation of Polyimide Film

Then, appropriate amounts of an additive and the base generator of the present invention are mixed with the polyimide precursor of formula (12) and the solution is stirred homogeneously under nitrogen. After that, the resin solution is applied on a copper foil by knife coating and then baked in an oven. The baking includes two stages: the first stage involving heating from room temperature to 120 to 170° C. in 20 to 50 minutes and curing for 30 to 90 minutes at 120 to 170° C., and the second stage involving heating up to 200 to 250° C. and curing for 60 to 240 minutes at 200 to 250° C. After curing, the copper foil is removed by etching to obtain a polyimide film.

The following examples will exemplify aspects of the present invention and explain the technical features of the present invention, but are not intended to confine the scope of the present invention. Both modification and equivalent arrangement made readily by anyone skilled in the art fall within the scope claimed by the present invention, which shall be defined by the appended claims.

EXAMPLE 1

Preparation of Base Generator According to the Present Invention

Base Generator Compound 1:

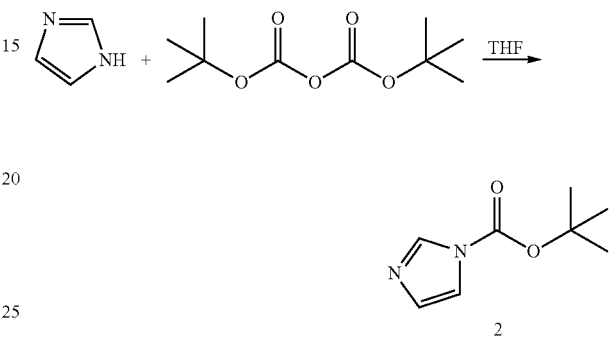

Under nitrogen, imidazole was dissolved in anhydrous tetrahydrofuran (THF), and an appropriate amount of di-tert-butyl dicarbonate was dropped slowly into the solution; then reaction was carried out for about 2 hours accompanied by effervescent and exothermic phenomena. After the reaction was completed, the solvent and tert-butyl alcohol byproduct were removed by vacuum reduced pressure concentration to provide compound 2 as white solid, with yield of about 95%.

Next, under nitrogen, compound 2 was dissolved in dichloromethane, and compound 3 (trimethyloxonium tetrafluoroborate) was dropped slowly into the solution at 0° C.; then reaction was carried out for about 2 hours at room temperature. After that, the solution was added to ether to generate a solid precipitate; then the solution was filtered and the obtained solid was rinsed with ether to provide compound 1 as white solid, with yield of about 70%.

EXAMPLE 2

Preparation of Base Generator According to the Present Invention

Base Generator Compound 6:

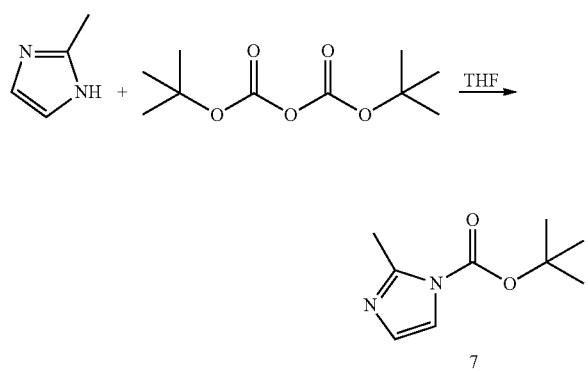

Under nitrogen, 2-methylimidazole was dissolved in anhydrous THF, and an appropriate amount of di-tert-butyl dicarbonate was dropped slowly into the solution; then reaction was carried out for about 2 hours accompanied by effervescent and exothermic phenomena. After the reaction was completed, the solvent and tert-butyl alcohol byproduct were removed by vacuum reduce pressure concentration to provide compound 7 as white solid, with the yield of about 89%.

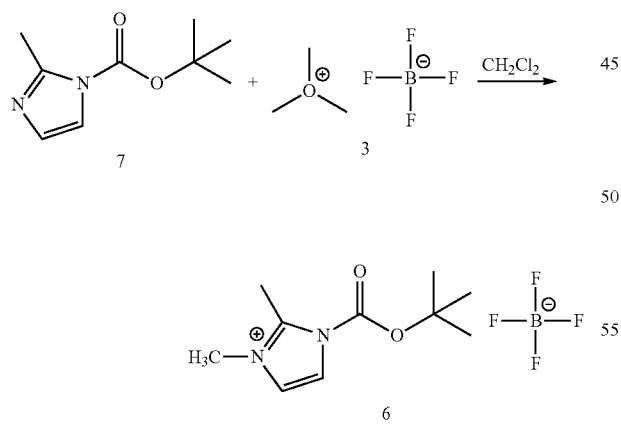

Next, under nitrogen, compound 7 was dissolved in dichloromethane, and compound 3 was dropped slowly into the solution at 0° C.; then reaction was carried out for about 2 hours at room temperature. After that, the solution was added to ether to generate a solid precipitate; then the solution was filtered and the obtained solid was rinsed with diethyl ether to provide compound 6 as white solid, with yield of about 73%.

EXAMPLE 3

Preparation of Base Generator According to the Present Invention

Base Generator Compound 8:

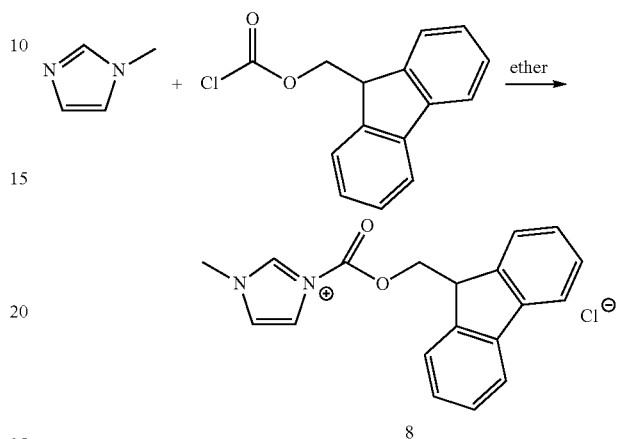

Under nitrogen, 9-fluorenylmethyl chloroformate was dissolved in ether, and an appropriate amount of 1-methyl imidazole was dropped slowly into the solution under ice bath condition. The solution was stirred continuously for about half an hour under ice bath condition, and then reaction was carried out for about 2 hours at room temperature. After that, the solvent was removed by vacuum reduced pressure concentration; and crystallization was carried out with ethanol for purification to provide compound 8 as yellow crystalline solid, with yield of about 95%.

EXAMPLE 4

Preparation of Base Generator According to the Present Invention

Base Generator Compound 9:

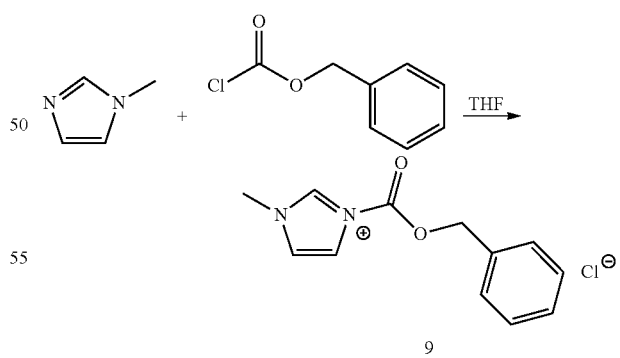

Under nitrogen, benzyl chloroformate was dissolved in ether, and an appropriate amount of 1-methyl imidazole was dropped slowly into the solution under ice bath condition. The solution was stirred continuously for about half an hour under ice bath, and then reaction was carried out for about 2 hours at room temperature. After that, the solvent was removed by vacuum reduced pressure concentration; and crystallization was carried out with ethanol for purification, to provide compound 9 as light yellow crystalline solid, with yield of about 85%.

EXAMPLE 5

Preparation of Base Generator According to the Present Invention

Base Generator Compound 10:

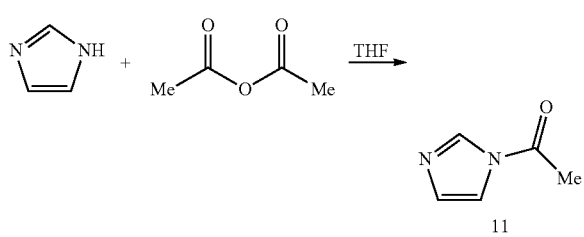

Under nitrogen, imidazole was dissolved in anhydrous THF, and an appropriate amount of acetic anhydride was dropped slowly into the solution; then reaction was carried out for about half an hour accompanied by exothermic phenomena. After the reaction was completed, the solvent was removed by vacuum reduced pressure concentration to generate a solid product. Then, the obtained solid was rinsed with n-hexane and filtered to provide compound 11 as white solid, with yield of about 98%.

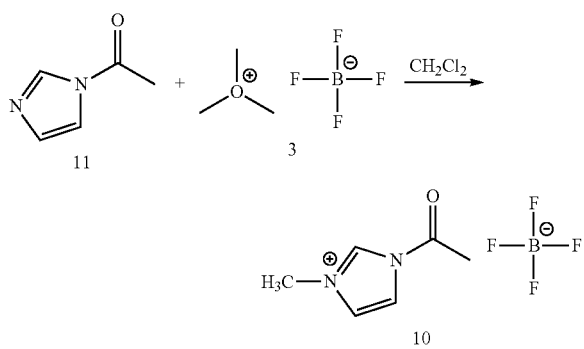

Next, under nitrogen, compound 11 was dissolved in dichloromethane, and compound 3 was dropped slowly into the solution at 0° C.; then reaction was carried out for about 2 hours at room temperature. After that, the solution was added to ether to generate a solid precipitate, and the solution was filtered and the obtained solid was rinsed with ether to provide compound 10 as white solid, with yield of about 81%.

EXAMPLE 6

Preparation of Polyimide Film with the Base Generator According to the Present Invention (a) Preparation of Polyimide Precursor Polyimide precursor 4: 29.42 g (0.1 mole) 3,3',4,4'-biphenyltetracarboxylic dianhydride (BPDA) was dissolved in 200 g NMP, and the solution was heated to 50° C. and stirred for 2 hours for reaction. Then, 13.01 g (0.01 mole) 2-hydroxyethyl methacrylate (HEMA) was dropped slowly into the solution and stirred at a fixed temperature of 50° C. for reaction for 2 hours. After reaction, 10.814 g (0.1 mole) p-phenylenediamine (pPDA) was added to the solution, and after complete dissolution, the solution was stirred at a fixed temperature of 50° C. for reaction for 6 hours to provide the polyimide precursor 4.

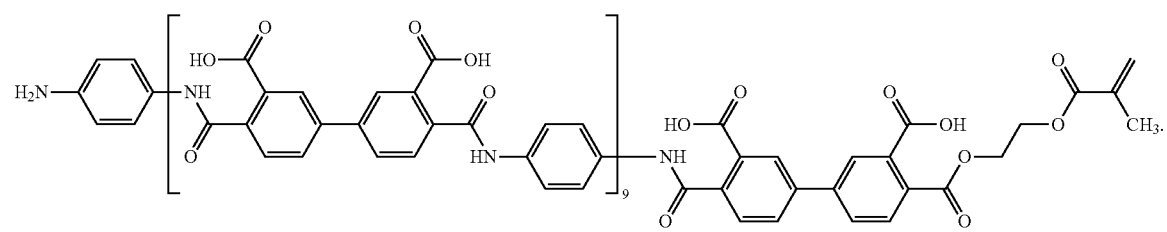

(b) Preparation of Polyimide Film 100 parts by weight of the polyimide precursor 4 and 1 part by weight of the base generator compound 1 obtained from Example 1 were mixed homogeneously under nitrogen. The mixture was applied uniformly on a copper foil by knife coating and then baked in an oven. The baking includes two stages: the first stage involving heating from room temperature to 150° C. in 35 minutes and curing for 30 minutes at 150° C., and the second stage involving heating from 150° C. to 200° C. and curing for 120 minutes at 200° C. (the final curing temperature of 200° C. can be changed to 250° C., 300° C. or higher, and the heating rates can all be 3.5° C./minute). After curing, the copper foil was removed by etching to provide the polyimide film.

EXAMPLE 7

Preparation of Polyimide Film with the Base Generator According to the Present Invention (a) Preparation of Polyimide Precursor Polyimide precursor 5: 29.42 g (0.1 mole) BPDA was dissolved in about 880 g NMP, and the solution was heated to 50° C. and stirred for 2 hours for reaction. Then, 3.71 g (0.05 mole) n-butanol was dropped slowly into the solution and stirred for 4 hours at a fixed temperature of 50° C. for reaction. After reaction, 30.01 g (0.15 mole) 4,4'-oxydianiline (ODA) was added to the solution at room temperature, and after complete dissolution, 37.85 g (0.35 mole) pPDA was added to the solution, and after complete dissolution, 117.68 g (0.4 mole) BPDA was added to the solution. Then, the solution was stirred at a fixed temperature of 50° C. for 8 hours for reaction to provide the polyimide precursor 5.

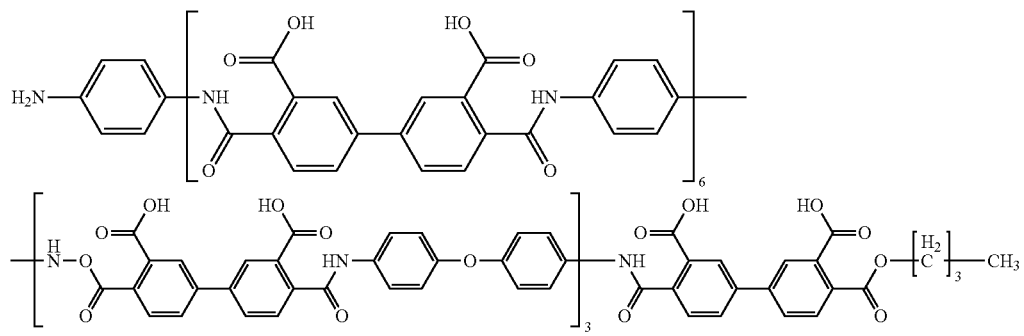

(b) Preparation of Polyimide Film

After 100 parts by weight of the polyimide precursor 5 and 1 part by weight of the base generator compound 1 obtained from Example 1 were mixed homogeneously under nitrogen, the same method as that in Example 6(b) was used to prepare a polyimide film.

EXAMPLE 8

Preparation of Polyimide Film with the Base Generator According to the Present Invention After 100 parts by weight of the polyimide precursor 4 obtained from Example 6 and 1 part by weight of the base generator compound 6 obtained from Example 2 were mixed homogeneously under nitrogen, the same method as that in Example 6(b) was used to prepare a polyimide film.

EXAMPLE 9

Preparation of Polyimide Film with the Base Generator According to the Present Invention After 100 parts by weight of the polyimide precursor 5 obtained from Example 7 and 1 part by weight of the base generator compound 6 obtained from Example 2 were mixed homogeneously under nitrogen, the same method as that in Example 6(b) was used to prepare a polyimide film.

Example 10

Preparation of Polyimide Film with the Base Generator According to the Present Invention After 100 parts by weight of the polyimide precursor 4 obtained from Example 6 and 1 part by weight of the base generator compound 8 obtained from Example 3 were mixed homogeneously under nitrogen, the same method as that in Example 6(b) was used to prepare a polyimide film.

EXAMPLE 11

Preparation of Polyimide Film with the Base Generator According to the Present Invention After 100 parts by weight of the polyimide precursor 5 obtained from Example 7 and 1 part by weight of the base generator compound 8 obtained from Example 3 were mixed homogeneously under nitrogen, the same method as that in Example 6(b) was used to prepare a polyimide film.

EXAMPLE 12

Preparation of Polyimide Film with the Base Generator According to the Present Invention After 100 parts by weight of the polyimide precursor 4 obtained from Example 6 and 1 part by weight of the base generator compound 9 obtained from Example 4 were mixed homogeneously under nitrogen, the same method as that in Example 6(b) was used to prepare a polyimide film.

EXAMPLE 13

Preparation of Polyimide Film with the Base Generator According to the Present Invention After 100 parts by weight of the polyimide precursor 5 obtained from Example 7 and 1 part by weight of the base generator compound 9 obtained from Example 4 were mixed homogeneously under nitrogen, the same method as that in Example 6(b) was used to prepare a polyimide film.

COMPARATIVE EXAMPLE 1

Preparation of Polyimide with Conventional Base Generator

Conventional base generator 12:

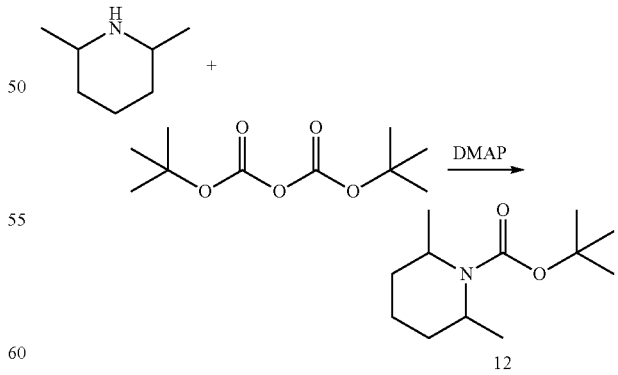

According to a synthetic method (Mitsuru Ueda, Chemistry Letters, 2005, Vol. 34, p. 1372-1373), 2,6-dimethyl-piperidine, di-tert-butyl dicarbonate and 4-(dimethylamino)pyridine (DMAP) were mixed together and heated at a temperature of 50° C. for 12 hours, and then the mixture was washed with water and extracted prior to reduced pressure distillation, to provide a colorless liquid, with yield of about 59%.

Next, 1 part by weight of conventional base generator compound 12 and 100 parts by weight of the polyimide precursor 4 obtained from Example 6 were mixed homogeneously under nitrogen, and the same method as that in Example 6(b) was used to prepare a polyimide film.

COMPARATIVE EXAMPLE 2

Preparation of Polyimide with Conventional Base Generator

After 100 parts by weight of the polyimide precursor 5 obtained from Example 7 and 1 part by weight of the conventional base generator compound 12 were mixed homogeneously under nitrogen, the same method as that in Example 6(b) was used to prepare a polyimide film.

COMPARATIVE EXAMPLE 3

Preparation of Polyimide without Base Generator

The polyimide precursor 4 obtained from Example 6 was applied onto a copper foil by direct knife coating, and then the same method as that in Example 6(b) was used to prepare a polyimide film.

COMPARATIVE EXAMPLE 4

Preparation of Polyimide without Base Generator

The polyimide precursor 5 obtained from Example 7 was applied onto a copper foil by direct knife coating, and then the same method as that in Example 6(b) was used to prepare a polyimide film.

Physical Property Testing of Polyimide Films

FIG. 1 shows a flow chart for physical property testing of polyimide films according to the present invention. Table 1 shows the properties of the polyimide films prepared from the polyimide precursor 4 obtained from Example 6.

TABLE 1

| Polyimide films | Final curing temperature (° C.) | $T_g^{(1)}$ (° C.) | $CTE^{(2)}$ (ppm) | $Td_{5\%}^{(3)}$ (° C.) |
|---|---|---|---|---|
| Example 6 | 200 | 362.55 | 2.77 | 425.40 |
| | 250 | 364.29 | 1.51 | 589.45 |
| | 300 | 365.68 | 1.05 | 598.20 |
| Example 8 | 200 | 350.42 | 3.53 | 427.40 |
| | 250 | 364.33 | 2.18 | 590.87 |
| | 300 | 365.15 | 1.49 | 599.71 |
| Example 10 | 200 | 353.18 | 4.44 | 399.70 |
| | 250 | 364.80 | 2.15 | 575.15 |
| | 300 | 366.14 | 1.17 | 587.58 |
| Example 12 | 200 | 360.43 | 2.13 | 407.15 |
| | 250 | 366.81 | 1.09 | 553.21 |
| | 300 | 366.88 | 0.98 | 561.18 |
| Comparative Example 1 | 200 | 345.15 | 3.24 | 352.46 |
| | 250 | 353.44 | 5.93 | 560.33 |
| | 300 | 361.33 | 3.22 | 599.33 |
| Comparative Example 3 | 200 | 205.25 | 6.31 | 330.45 |
| | 250 | 208.40 | 2.20 | 541.71 |
| | 300 | 301.82 | 2.95 | 540.30 |

TABLE 1-continued

| Polyimide films | Final curing temperature (° C.) | $T_g^{(1)}$ (° C.) | $CTE^{(2)}$ (ppm) | $Td_{5\%}^{(3)}$ (° C.) |
|---|---|---|---|---|
| | 350 | 352.90 | 1.89 | 539.25 |
| | 350$^{(4)}$ | 364.18 | 0.79 | 537.79 |

$^{(1)}$Glass transition temperature
$^{(2)}$Coefficient of thermal expansion
$^{(3)}$Pyrolytic temperature for 5% weight loss
$^{(4)}$Heating profile: heating from room temperature to 150° C. in 20 minutes, maintaining 150° C. for 120 minutes; then heating to 250° C. in 20 minutes, and maintaining 250° C. for 60 minutes (at a heating rate of 3.5° C./minute); then heating to 350° C. in 50 minutes and maintaining this temperature for 120 minutes.

Table 2 shows the properties of the polyimide films prepared from the polyimide precursor 5 obtained from Example 7.

TABLE 2

| Polyamide films | Final curing temperature (° C.) | $T_g^{(1)}$ (° C.) | $CTE^{(2)}$ (ppm) | $Td_{5\%}^{(3)}$ (° C.) |
|---|---|---|---|---|
| Example 7 | 200 | 330.91 | 16.41 | 435.13 |
| | 250 | 341.14 | 11.31 | 586.49 |
| | 300 | 343.14 | 9.62 | 587.60 |
| Example 9 | 200 | 318.51 | 16.38 | 430.00 |
| | 250 | 337.15 | 13.11 | 580.30 |
| | 300 | 340.55 | 11.52 | 579.13 |
| Example 11 | 200 | 324.15 | 15.99 | 418.18 |
| | 250 | 339.00 | 12.00 | 579.80 |
| | 300 | 343.29 | 10.11 | 584.54 |
| Example 13 | 200 | 333.23 | 15.73 | 420.83 |
| | 250 | 344.18 | 11.19 | 543.15 |
| | 300 | 343.57 | 11.00 | 569.18 |
| Comparative Example 2 | 200 | 313.43 | 18.15 | 358.15 |
| | 250 | 334.77 | 13.17 | 565.61 |
| | 300 | 340.67 | 11.38 | 577.33 |
| Comparative Example 4 | 200 | 221.25 | 19.58 | 418.79 |
| | 250 | 280.68 | 16.42 | 579.97 |
| | 300 | 307.49 | 12.87 | 565.30 |
| | 350 | 337.75 | 10.26 | 570.13 |
| | 350$^{(4)}$ | 340.15 | 10.15 | 580.29 |

$^{(1)}$Glass transition temperature
$^{(2)}$Coefficient of thermal expansion
$^{(3)}$Pyrolytic temperature for 5% weight loss
$^{(4)}$Heating profile: heating from room temperature to 150° C. in 20 minutes, maintaining 150° C. for 120 minutes; then heating to 250° C. in 20 minutes, and maintaining 250° C. for 60 minutes (at a heating rate of 3.5° C./minute); then heating to 350° C. in 50 minutes and maintaining this temperature for 120 minutes.

The glass transition temperature and the coefficient of thermal expansion were measured by thermo-mechanical analyzer TA TMA Q-400. The coefficient of thermal expansion of the polyimide film was measured at a heating rate of 10° C./minute at from 40 to 300° C. in nitrogen according to ASTM-D3386.

The temperature for 5% weight loss of the polyimide film relative to the initial weight of the polyimide film was employed as the pyrolysis temperature Tdss. The pyrolysis temperature for 5% weight loss ($Td_{5\%}$) was measured by thermogravimetric analyzer TA Q-5000 at a heating rate of 20° C./minute from 30 to 900° C.

Films Prepared from Polyimide Precursor 4

It can be seen from Table 1 that the polyimide films prepared from the polyimide precursor composition according to the present invention exhibit excellent thermal and mechanical properties even when they were cured at low temperature of 200° C., and have higher glass transition temperatures than those of Comparative Example 3 (the polyimide film without addition of a base generator) and Comparative Example 1, demonstrating that the present invention can effectively promote cyclization of polyamic acid. In addition, most of the films obtained from the examples of the present invention have a lower coefficient of thermal expansion than that of the films obtained from the comparative examples.

In Comparative Example 3 (polyimide film without addition of a base generator), the glass transition temperature was raised higher than 350° C. only if the curing temperature was higher than 350° C.; and the glass transition temperature was raised higher than 360° C. only if the heating profile was changed (see the final curing temperature 350° C. in Table 1). Nevertheless, the glass transition temperatures of the polyimide films obtained from the polyimide precursor 4 of the present invention were raised to 360° C. only with the curing temperature of 250° C.

It can be seen from the data from the thermogravimetric analyzer that, due to addition of the base generator of the present invention, the cyclization rate of polyimide was increased and the pyrolytic temperature for 5% weight loss was also raised.

Films Prepared from Polyimide Precursor 5

It can be seen from Table 2 that the physical properties of the films prepared from polyimide precursor 5 were similar to those from polyimide precursor 4. From this, it can be concluded that the base generators according to the present invention are useful for various types of polyimide precursors.

Given the above, compared to conventional polyimide films, the polyimide films prepared from the precursor composition comprising the polyimide precursor and the base generator precursor of the present invention by curing at a low temperature have a higher rate of cyclization than that of the comparative examples, and are advantageous in terms of glass transition temperature, coefficient of thermal expansion and pyrolytic temperature for 5% weight loss, thus enabling use in a wide range of applications.

What is claimed is:

1. A polyimide precursor composition comprising (a) a polyimide precursor, and (b) a thermal base generator having the structure of formula (1):

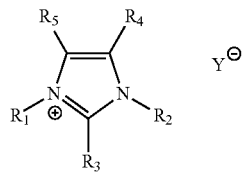

(1)

wherein $R_1$ is linear or branched $C_1$-$C_6$ alkyl, linear or branched $C_1$-$C_6$ haloalkyl, linear or branched $C_1$-$C_6$ alkyl substituted with one or more $C_6$-$C_{14}$ aryl,

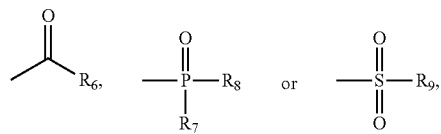

$R_2$ is linear or branched $C_1$-$C_6$ alkyl substituted with one or more $C_6$-$C_{14}$ aryl,

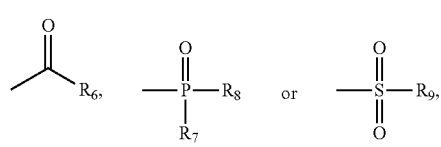

wherein $R_6$ is linear or branched $C_1$-$C_6$ alkyl, linear or branched $C_1$-$C_6$ haloalkyl, linear or branched $C_1$-$C_8$ alkoxy unsubstituted or substituted with one or more $C_6$-$C_{14}$ aryl, or —$NR_{10}R_{11}$, and $R_7$, $R_8$, $R_9$, $R_{10}$ and $R_{11}$ are the same or different, and are each independently H, linear or branched $C_1$-$C_{14}$ alkyl unsubstituted or substituted with one or more $C_6$-$C_{14}$ aryl, or $C_6$-$C_{14}$ aryl;

$R_3$, $R_4$ and $R_5$ are the same or different, and are each independently H, linear or branched $C_1$-$C_6$ alkyl unsubstituted or substituted with one or more $C_6$-$C_{14}$ aryl, linear or branched $C_1$-$C_6$ hydroxyalkyl, linear or branched $C_1$-$C_6$ cyanoalkyl, or $C_6$-$C_{14}$ aryl; and $Y^\ominus$ is an anionic group.

2. The precursor composition according to claim 1, wherein a weight ratio of component (a) to component (b) ranges from 2000:1 to 5:1.

3. The precursor composition according to claim 2, wherein a weight ratio of component (a) to component (b) ranges from 200:1 to 10:1.

4. The precursor composition according to claim 1, wherein $R_1$ is methyl, ethyl, propyl, butyl or selected from a group consisting of:

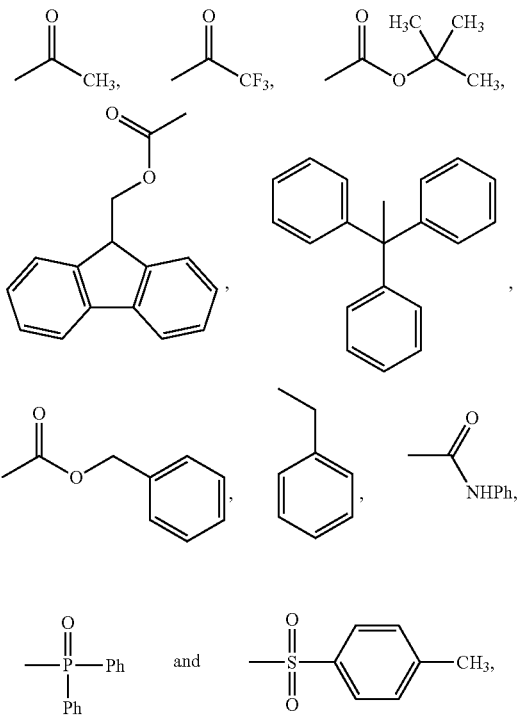

and $R_2$ is from the group consisting of

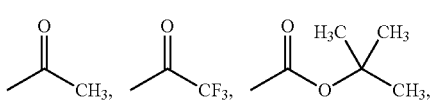

-continued

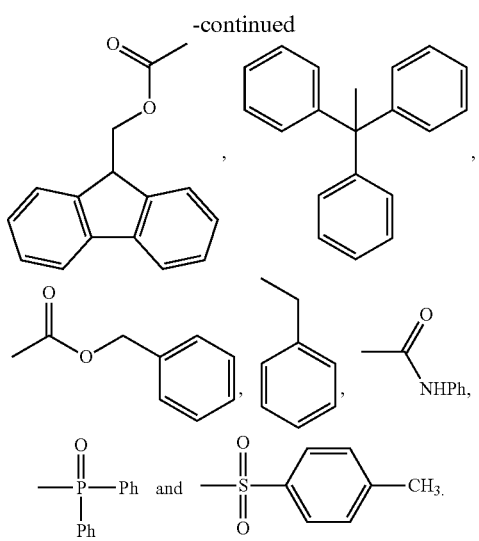

5. The precursor composition according to claim 1, wherein $R_1$ is methyl, ethyl or selected from a group consisting of:

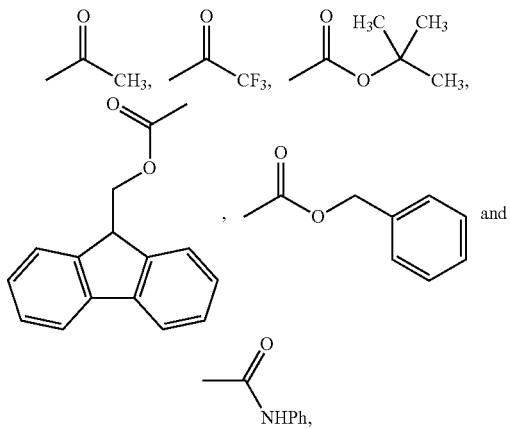

and
$R_2$ is selected from the group consisting of

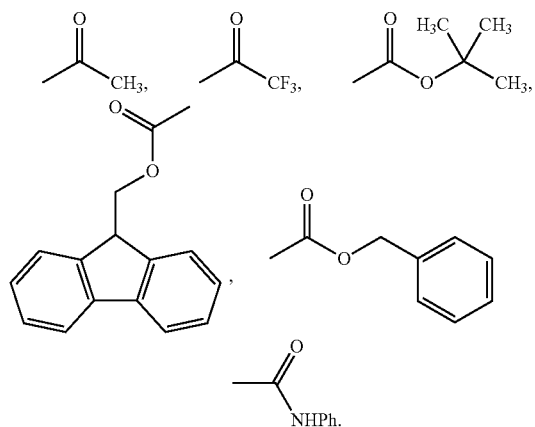

6. The precursor composition according to claim 1, wherein $R_3$, $R_4$ and $R_5$ are the same or different and are each independently H, methyl, ethyl, n-propyl, isopropyl, n-butyl, isobutyl, tert-butyl, pentyl, hexyl, hydroxymethyl, hydroxyethyl, hydroxypropyl, hydroxybutyl, hydroxypentyl, hydroxyhexyl, cyanomethyl, cyanoethyl, cyanopropyl, cyanobutyl, cyanopentyl, cyanohexyl, phenyl, benzyl or diphenylmethyl.

7. The precursor composition according to claim 1, wherein $R_3$, $R_4$ and $R_5$ are the same or different and are each independently H, methyl, ethyl, n-propyl or isopropyl.

8. The precursor composition according to claim 1, wherein the anionic group is selected from a group consisting of halide ion, sulfate, nitrate, phosphate, sulfonate, carbonate, tetrafluoborate, borate, chlorate, iodate, hexafluorophosphate, perchlorate, trifluoromethanesulfonate, trifluoroacetate, acetate, tert-butylcarbonate, $(CF_3SO_2)_2N^-$ and tert-butyloxy.

9. The precursor composition according to claim 1, wherein the anionic group is a halide ion or tetrafluoroborate.

10. The precursor composition according to claim 1, wherein the polyimide precursor is selected from a group consisting of:

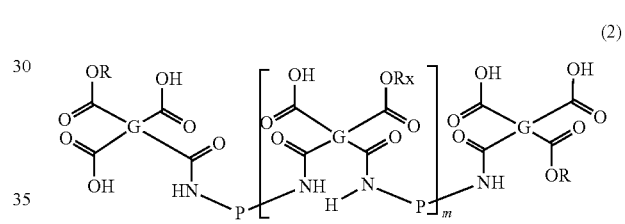

(2)

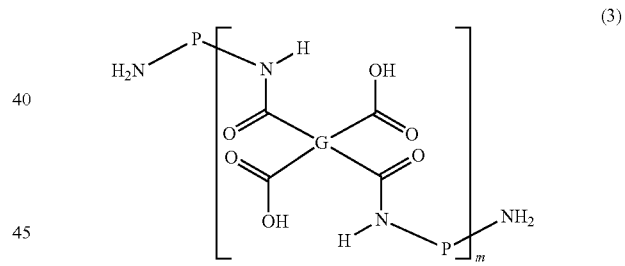

(3)

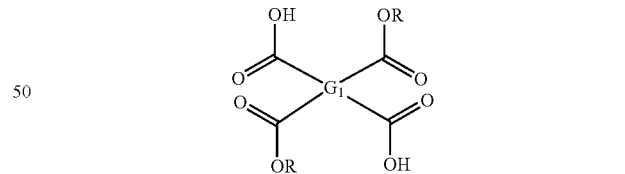

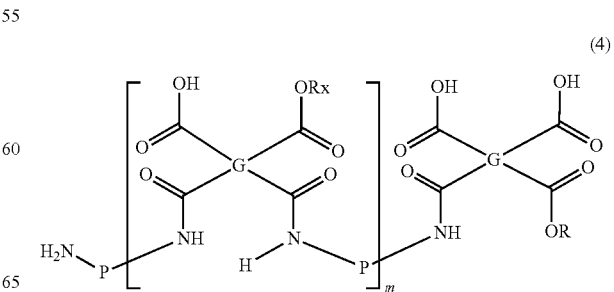

(4)

(5)

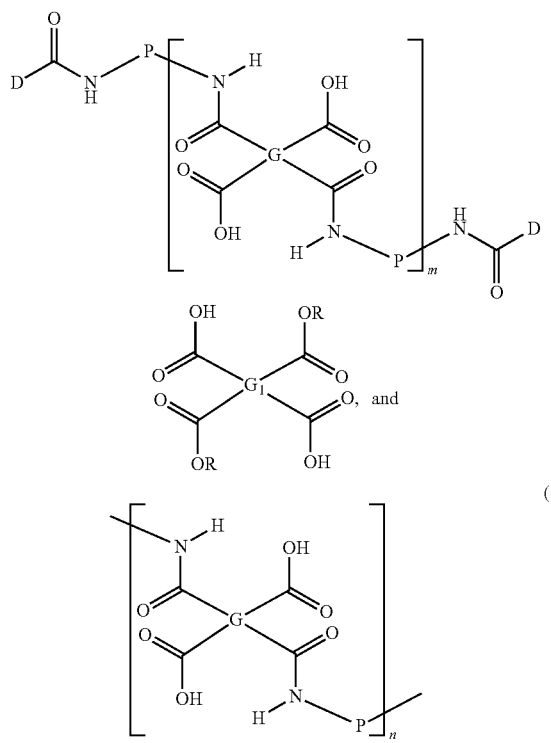

(6)

wherein,
- G and $G_1$ are the same or different and are each independently a tetravalent organic group;
- each P independently represents a divalent organic group;
- each R independently represents linear or branched $C_1$-$C_{14}$ alkyl, $C_6$-$C_{14}$ aryl, $C_6$-$C_{14}$ aralkyl, a phenolic group or an ethylenically unsaturated group;
- each $R_x$ independently represents H or an ethylenically unsaturated group;
- each D independently represents a nitrogen-containing heterocyclic group or a OR* group, wherein R* is linear or branched $C_1$-$C_{20}$ alkyl;
- each m is an integer from 0 to 100; and
- each n is an integer greater than 0.

11. The precursor composition according to claim 10, wherein the ethylenically unsaturated group is selected from a group consisting of ethenyl, propenyl, methylpropenyl, n-butenyl, isobutenyl, ethenylphenyl, propenylphenyl, propenyloxymethyl, propenyloxyethyl, propenyloxypropyl, propenyloxybutyl, propenyloxypentyl, propenyloxyhexyl, methylpropenyloxymethyl, methylpropenyloxyethyl, methylpropenyloxypropyl, methylpropenyloxybutyl, methylpropenyloxypentyl, methylpropenyloxyhexyl, a group of the following formula (7) and a group of the following formula (8):

(7)

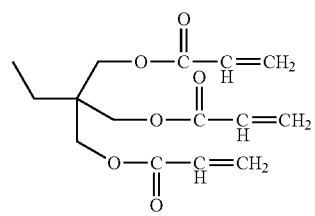

(8)

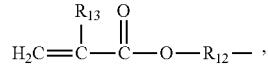

wherein $R_{12}$ is a phenylene, linear or branched $C_1$-$C_8$ alkylene, linear or branched $C_2$-$C_8$ alkenylene, $C_3$-$C_8$ cycloalkylene, or linear or branched $C_1$-$C_8$ hydroxylalkylene; and $R_{13}$ is hydrogen or linear or branched $C_1$-$C_4$ alkyl.

12. The precursor composition according to claim 10, wherein the tetravalent organic group is selected from a group consisting of:

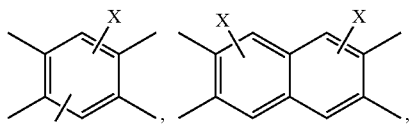

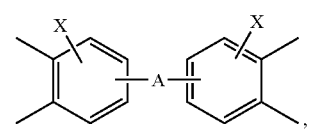

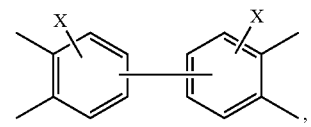

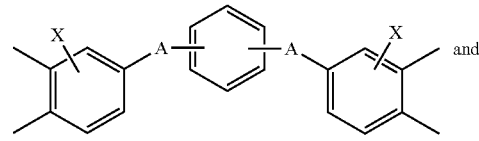

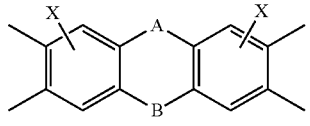

wherein X is each independently hydrogen, halogen, linear or branched $C_1$-$C_4$ perfluoroalkyl or linear or branched $C_1$-$C_4$ alkyl, and A and B are each independently a covalent bond, linear or branched $C_1$-$C_4$ alkyl, linear or branched $C_1$-$C_4$ perfluoroalkyl, alkoxy, silanyl, oxygen, sulfur, carbonyl, carboxylate, sulfonyl, phenyl, biphenyl, or

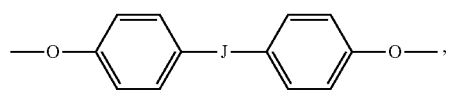

wherein J is —O—, —$SO_2$—, —$CH_2$—, $C(CF_3)_2$ or $C(CH_3)_2$.

13. The precursor composition according to claim 10, wherein the tetravalent organic group is selected from a group consisting of:
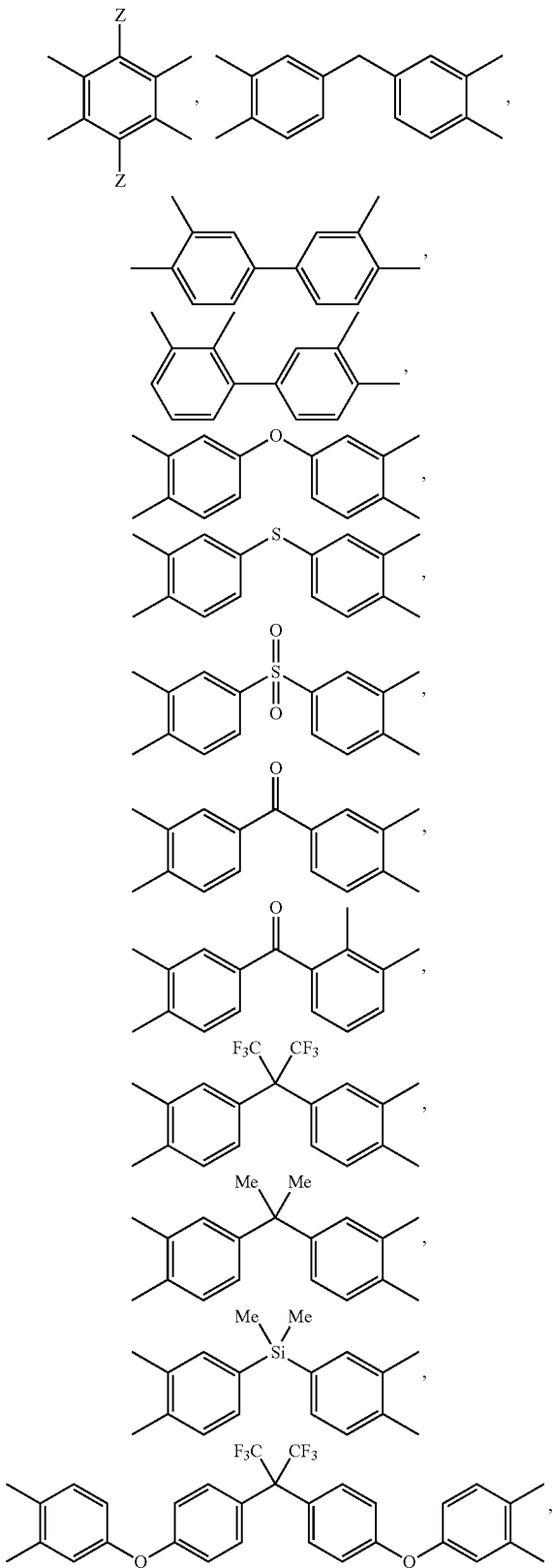
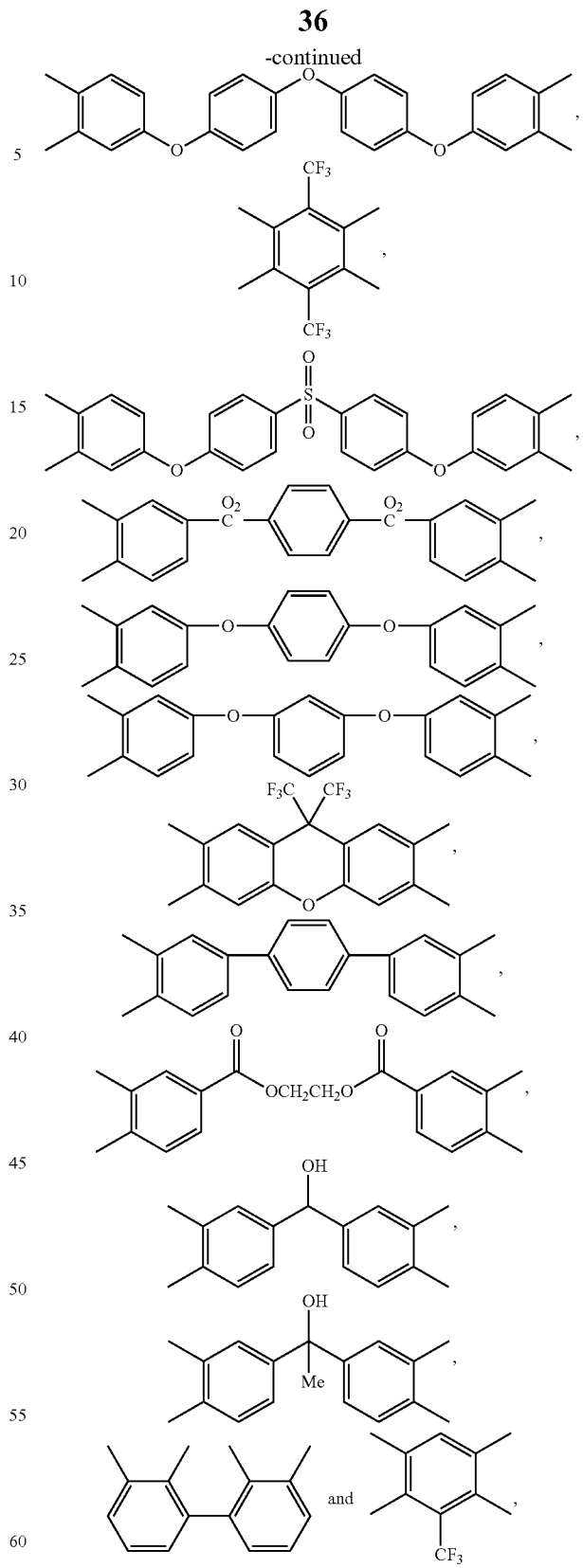
wherein Z is hydrogen or halogen.
14. The precursor composition according to claim 10, wherein the tetravalent organic group is selected from a group consisting of:

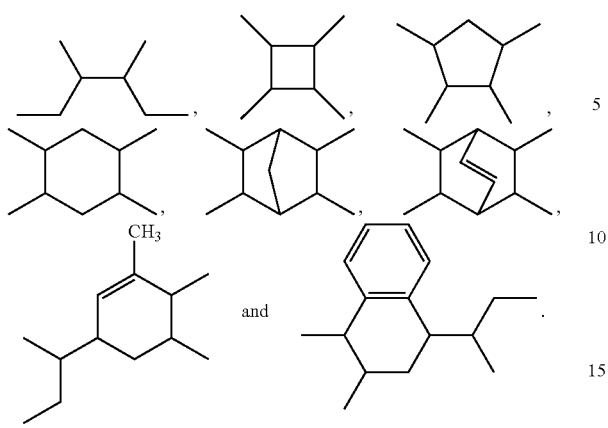

15. The precursor composition according to claim 10, wherein the divalent organic group is selected from a group consisting of:

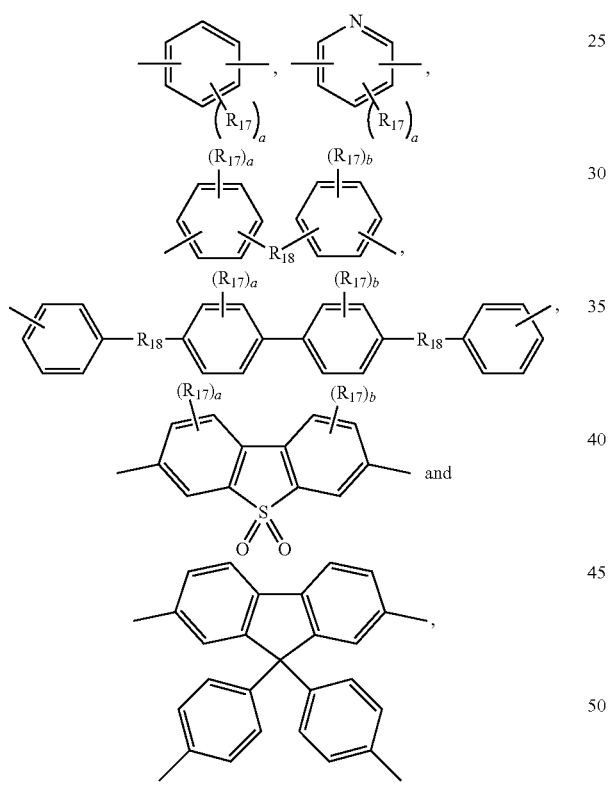

wherein, $R_{17}$ is each independently H, $C_1$-$C_4$ alkyl, $C_1$-$C_4$ perfluoroalkyl, methoxy, ethoxy, halogen, OH, COOH, $NH_2$ or SH;

each a is independently an integer of 0 to 4;

each b is independently an integer of 0 to 4; and $R_{18}$ is a covalent bond or a group selected from:

—O—, —S—, —$CH_2$—, —$S(O)_2$—,

-continued

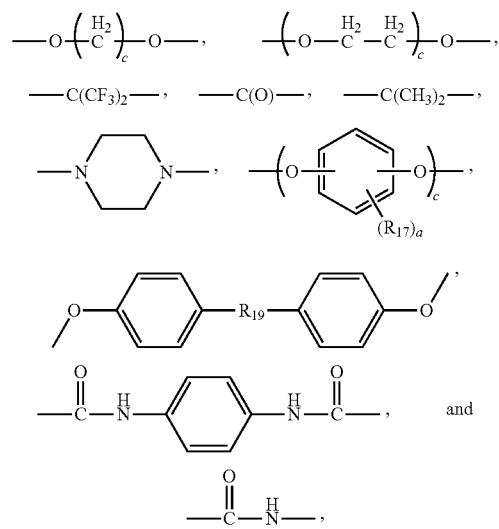

wherein, c and d are each independently an integer from 0 to 20;

$R_{17}$ and a are as defined above; and $R_{19}$ is —$S(O)_2$—, —C(O)—, a covalent bond or linear or branched $C_1$-$C_{18}$ alkyl.

16. The precursor composition according to claim 10, wherein the divalent organic group is selected from a group consisting of:

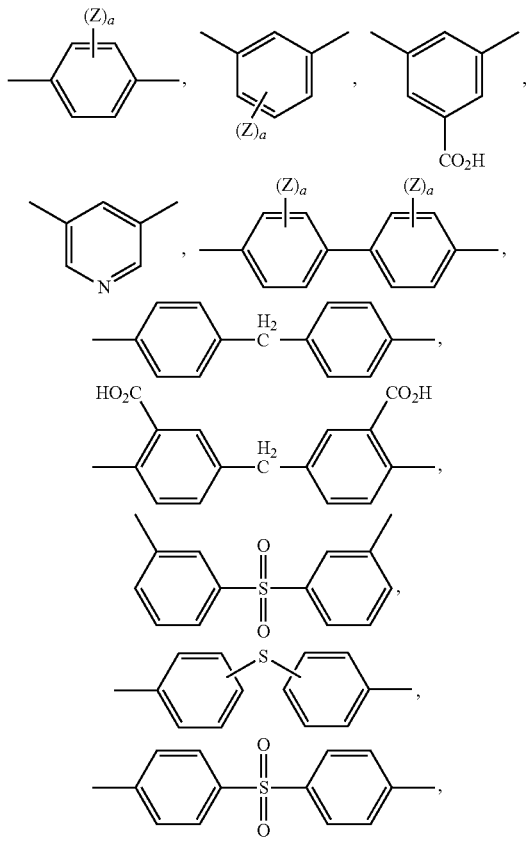

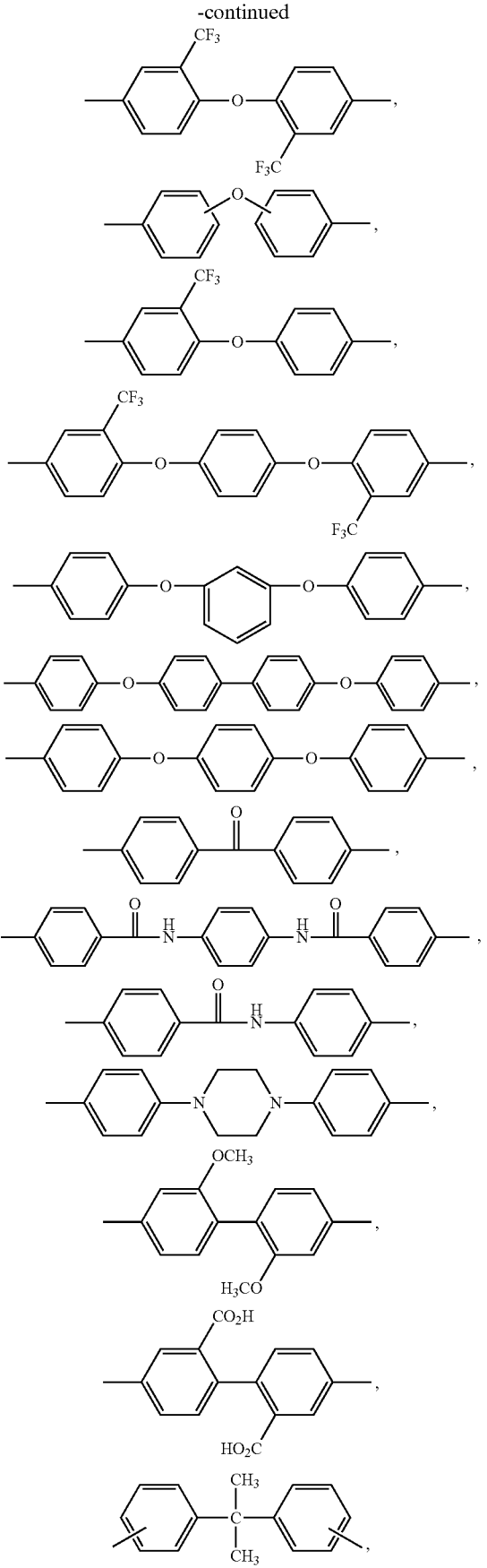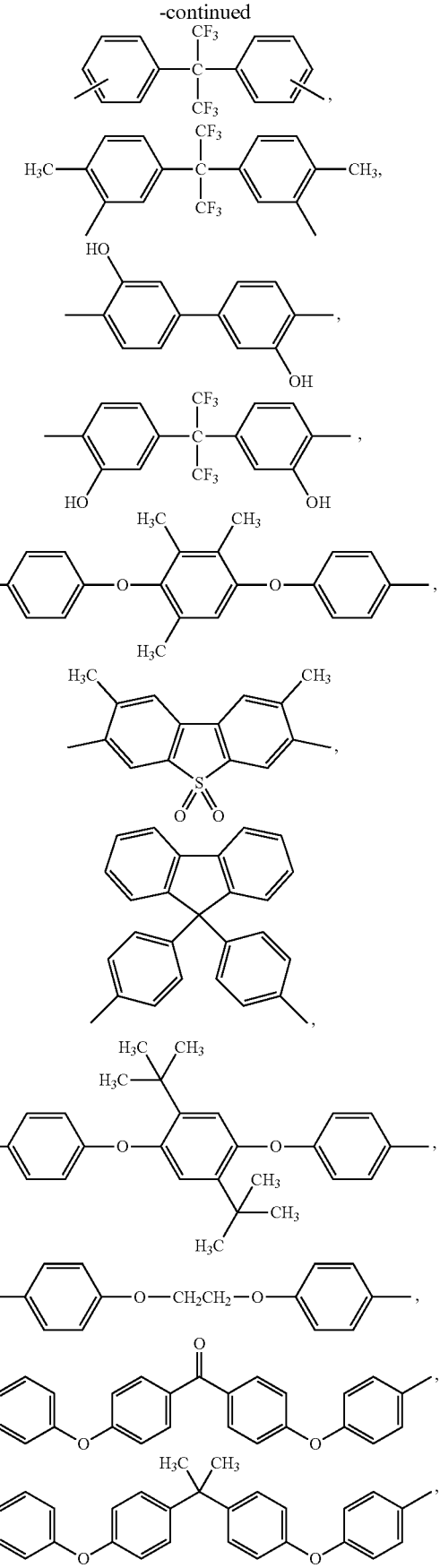

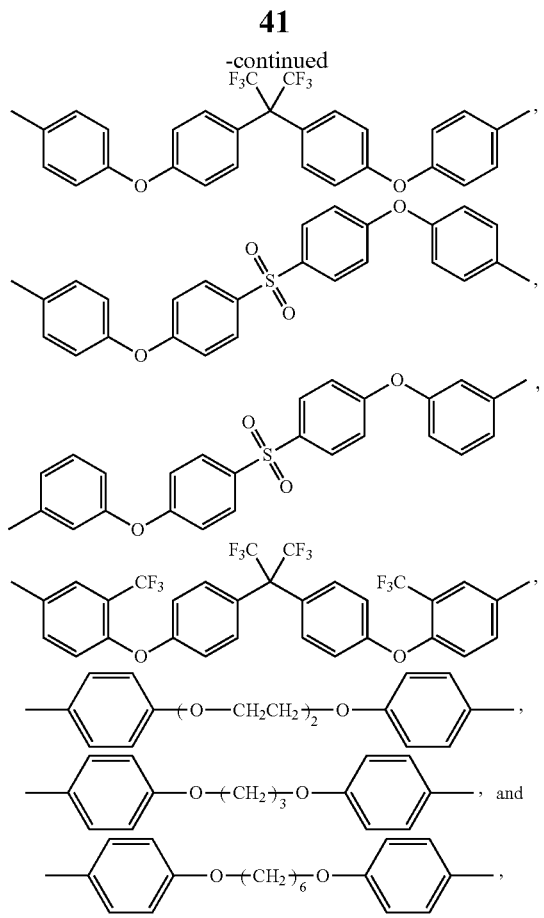

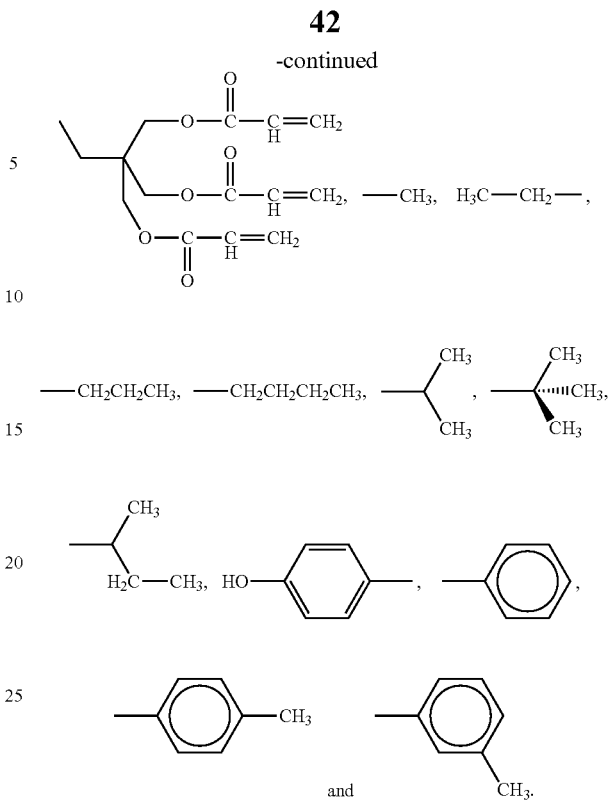

wherein
each of a is independently an integer of 0 to 4; and
each Z is independently hydrogen, methyl, trifluoromethyl or halogen.

17. The precursor composition according to claim 10, wherein the divalent organic group is:

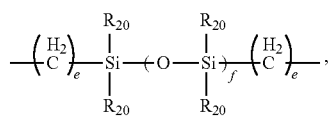

wherein each $R_{20}$ is independently H, methyl or ethyl; and e and f are each independently an integer greater than 0.

18. The precursor composition according to claim 10, wherein R is selected from a group consisting of:

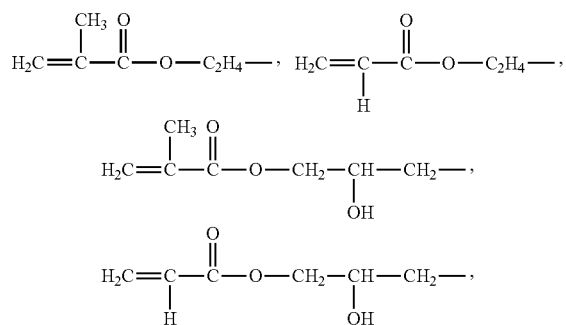

19. The precursor composition according to claim 1 further comprising a polar aprotic solvent selected from a group consisting of N-methylpyrrolidone, dimethyl acetamide, dimethyl formamide, dimethyl sulfoxide, toluene, xylene, propylene glycol methyl ether (PGME), propylene glycol methyl ether acetate (PGMEA), γ-butyrolactone (GBL), tetraethylene glycol dimethyl ether (TGDE) and a combination thereof.

20. The precursor composition according to claim 1, which is for use in the preparation of polyimide.

21. A polyimide prepared by polymerization of the polyimide precursor composition according to claim 1.

22. A method of preparing polyimide, which comprises polymerization of the polyimide precursor composition according to claim 1 by low temperature imidization.

23. The method according to claim 22, wherein the low temperature imidization is carried out at a temperature of not higher than 250° C.

24. The method according to claim 22, wherein the low temperature imidization is carried out at a temperature of not higher than 200° C.

25. The method according to claim 1, wherein $R_1$ and $R_2$ are the same or different and are each independently linear or branched $C_1$-$C_6$ alkyl substituted with one or more $C_6$-$C_{14}$ aryl,

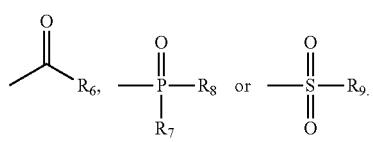

26. The precursor composition according to claim 1, wherein $R_1$ is linear or branched $C_1$-$C_6$ alkyl,

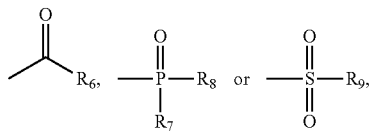

wherein $R_6$ is linear or branched $C_1$-$C_6$ alkyl, linear or branched $C_1$-$C_6$ haloalkyl, linear or branched $C_1$-$C_8$ alkoxy unsubstituted or substituted with one or more $C_6$-$C_{14}$ aryl, or —$NR_{10}R_{11}$; and $R_7$, $R_8$, $R_9$, $R_{10}$ and $R_{11}$ are the same or different and are each independent H, linear or branched $C_1$-$C_{14}$ alkyl, or $C_6$-$C_{14}$ aryl; $R_2$ is

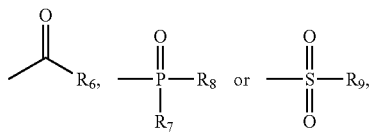

wherein $R_6$ is linear or branched $C_1$-$C_6$ alkyl, linear or branched $C_1$-$C_6$ haloalkyl, linear or branched $C_1$-$C_8$ alkoxy unsubstituted or substituted with one or more $C_6$-$C_{14}$ aryl, or —$NR_{10}R_{11}$; and $R_7$, $R_8$, $R_9$, $R_{10}$ and $R_{11}$ are the same or different and are each independent H, linear or branched $C_1$-$C_{14}$ alkyl, or $C_6$-$C_{14}$ aryl.

* * * * *